(12) United States Patent
Khan et al.

(10) Patent No.: US 11,472,779 B1
(45) Date of Patent: Oct. 18, 2022

(54) ONE-POT SYNTHESIS OF HYDROGEN-BONDED ORGANIC FRAMEWORKS

(71) Applicant: KING FAHD UNIVERSITY OF PETROLEUM AND MINERALS, Dhahran (SA)

(72) Inventors: Mohd Yusuf Khan, Dhahran (SA); Abuzar Khan, Dhahran (SA); Aasif Helal, Dhahran (SA); Zain H. Yamani, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 17/743,531

(22) Filed: May 13, 2022

(51) Int. Cl.
 *C07D 251/54* (2006.01)
 *C07C 211/51* (2006.01)
 *C07D 249/14* (2006.01)

(52) U.S. Cl.
 CPC .......... *C07D 251/54* (2013.01); *C07C 211/51* (2013.01); *C07D 249/14* (2013.01); *C07B 2200/13* (2013.01)

(58) Field of Classification Search
 CPC ... C07D 251/54; C07D 249/14; C07C 211/51; C07B 2200/13
 USPC ....................................................... 544/200
 See application file for complete search history.

(56) References Cited

FOREIGN PATENT DOCUMENTS

| CN | 113150305 A | 7/2021 |
| EP | 3 871 768 A1 | 9/2021 |
| WO | WO 2020/252536 A1 | 12/2020 |

OTHER PUBLICATIONS

Svetlana A. Kuznetsova, et al., "The charge-assisted hydrogen-bonded organic framework (CAHOF) self-assembled from the conjugated acid of tetrakis(4-aminophenyl)methane and 2,6-naphthalenedisulfonate as a new class of recyclable Brønsted acid catalysts", Beilstein Journal of Organic Chemistry, vol. 16, May 26, 2020, pp. 1124-1134.

Wei Yang, et al., "Highly Interpenetrated Robust Microporous Hydrogen-Bonded Organic Framework for Gas Separation", Crystal Growth & Design, vol. 17, No. 11, Oct. 23, 2017, pp. 6132-6137 (Supporting Information only).

Jie Luo, et al., "Hydrogen-bonded organic frameworks: design, structures and potential applications", CRYSTENGCOMM, vol. 20, Issue 39, Jun. 29, 2018, pp. 5884-5898 (Abstract only).

*Primary Examiner* — Kristin A Vajda
(74) *Attorney, Agent, or Firm* — Oblon, McClelland, Maier & Neustadt, L.L.P.

(57) ABSTRACT

A hydrogen-bonded organic framework (HOF) and a method of making the HOF. The HOF has at least one amine substituted organic linker and at least one carboxylic acid-based organic linker. The HOF is prepared by dissolving the linkers separately in water and mixing the aqueous solutions, without using any organic solvents, additional catalysts, or any other reagents.

20 Claims, 21 Drawing Sheets

ONE-POT SYNTHESIS OF HYDROGEN-BONDED ORGANIC FRAMEWORKS

BACKGROUND

Technical Field

The present disclosure relates to hydrogen-bonded organic frameworks (HOFs) and methods of preparation thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Porous materials such as metal-organic frameworks (MOFs), covalent organic frameworks (COFs), and hydrogen-bonded organic frameworks (HOFs), are a new generation of materials that have developed rapidly in recent years. These materials offer high surface areas and high porosity with ability to control pore sizes depending on the application. Such materials have been used for purposes like gas storage, gas separation, chemical sensing, catalysis, and opto-electronics.

HOFs are a new class of crystalline, porous materials that show exceptional properties and are assembled from small organic molecules. They exhibit a non-metallic character, high crystallinity, solution processability, self-repair, and self-assembly. These properties are largely dependent upon the organic linker molecules that create reversible hydrogen bonding (H-bonding) interconnections. In addition to H-bonds, the HOF skeleton is further stabilized through other fundamental weak forces such as, van der waals interactions, C—H . . . π interactions, and dipole-dipole interactions. These exceptional features of HOFs can provide a diverse platform to explore a variety of multifunctional porous materials.

Currently, many common organic molecules have been reported for HOF synthesis, including diaminotriazine (DAT), carboxylic acids (—COOH), sulfonic acids (—$SO_3H$), pyrazole, imidazole, pyridine, and urea. The HOFs are commonly synthesized using organic solvents such as dimethylformamide (DMF), and tetrahydrofuran (THF). The present synthetic methods include toxic organic solvents, are complicated and usually involve a multistep process that requires additional efforts and attention.

WO2021/170775A1 discloses a method for making a hydrogen-bonded organic framework (HOF) comprising an organic linker with at least one hydroxyl group. It further discloses that the central atom in the functional groups is preferably a P, As, Sb, Si, Se, or Bi atom. In a preferred exemplary embodiment, the HOF is synthesized by reacting phenylphosphonic acid (PPA) and 5,10,15,20-tetrakis[p-phenylphosphonic acid] porphyrin (Hs-TPPA) in DMF/EtOH or DMF/MeOH, for 48 hours at 80° C. $H_8$TPPA is a complex molecule which requires a multi-step synthesis prior to manufacturing of the HOF. Thus, the process of WO'775A1 is complex, multi-step reaction which uses metalloids, post-transition metals, or phosphorous and organic solvents.

CN113150305A discloses a method preparing of porous hydrogen-bonded organic frameworks using hexamethylenetetramine and a variety of carboxylic acids such as fumaric acid, phthalic acid, isophthalic acid, terephthalic acid, adipic acid, trimesic acid, and polyacrylic acid. The HOFs are prepared by reacting hexamethylenetetramine with a carboxylic acid in an organic solvent such as ethyl alcohol to obtain the HOF.

In light of aforementioned drawbacks, it is one object of the present disclosure to provide a one-pot synthesis of HOFs without use of any organic solvent. The disclosed method of preparation is a more cost-effective, simpler, and an eco-friendly approach. The HOFs are synthesized in water without additional reagents or catalysts.

SUMMARY

In an exemplary embodiment, a one-pot method of making a hydrogen-bonded organic framework (HOF) is disclosed. The method comprises the steps of: dissolving trimesic acid in water at a temperature greater than 60° C. to form a first solution; dissolving an aromatic compound in water to form a second solution, wherein the aromatic compound is substituted with at least two amine groups; adding dropwise the second solution into the first solution at a temperature greater than 60° C. to form a synthetic solution; cooling the synthetic solution to below 50° C. forming a precipitate; and separating and drying the precipitate at a temperature of at least 60° C. to yield the HOF; wherein the first and second solutions do not comprise an organic solvent.

In some embodiments, the first solution consists of water and trimesic acid.

In some embodiments, the second solution consists of water and the aromatic compound.

In some embodiments, the aromatic compound is selected from a group consisting of guanazole, melamine and p-phenylenediamine.

In some embodiments, the aromatic compound to trimesic acid molar ratio is 1:1 to 5:1.

In some embodiments, the temperature of the first solution during the dropwise addition of the second solution does not vary by more than 5° C.

In some embodiments, the first solution during the dropwise addition of the second solution is stirred at a rate of 600-800 rpm.

In some embodiments, the HOF is substantially crystalline.

In some embodiments, the HOF does not comprise non hydrogen-bonded aromatic compound.

In some embodiments, the aromatic compound is guanazole and the HOF has a sheet structure wherein the sheets form an intercrossed macroporous network with pores on a surface. In some embodiments, wherein the sheets have a thickness of 3-10 nm. In some embodiments, the pores have a diameter of 300-800 nm. In some embodiments, the HOF is stable up to 320° C.

In some embodiments, the aromatic compound is melamine, and the HOF has a sheet structure wherein the sheets form a flower morphology. In some embodiments, the sheets have a thickness of 25-40 nm. In some embodiments, the flowers have a diameter of 1-5 μm. In some embodiments, the HOF is stable up to 280° C.

In some embodiments, the aromatic compound is p-phenylenediamine and the HOF has a rod morphology wherein the rods comprise fused sheets. In some embodiments, the rods having a length of 0.5-4 μm. In some embodiments, the rods having a width of 200-600 nm.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Definitions

Figure 1A:
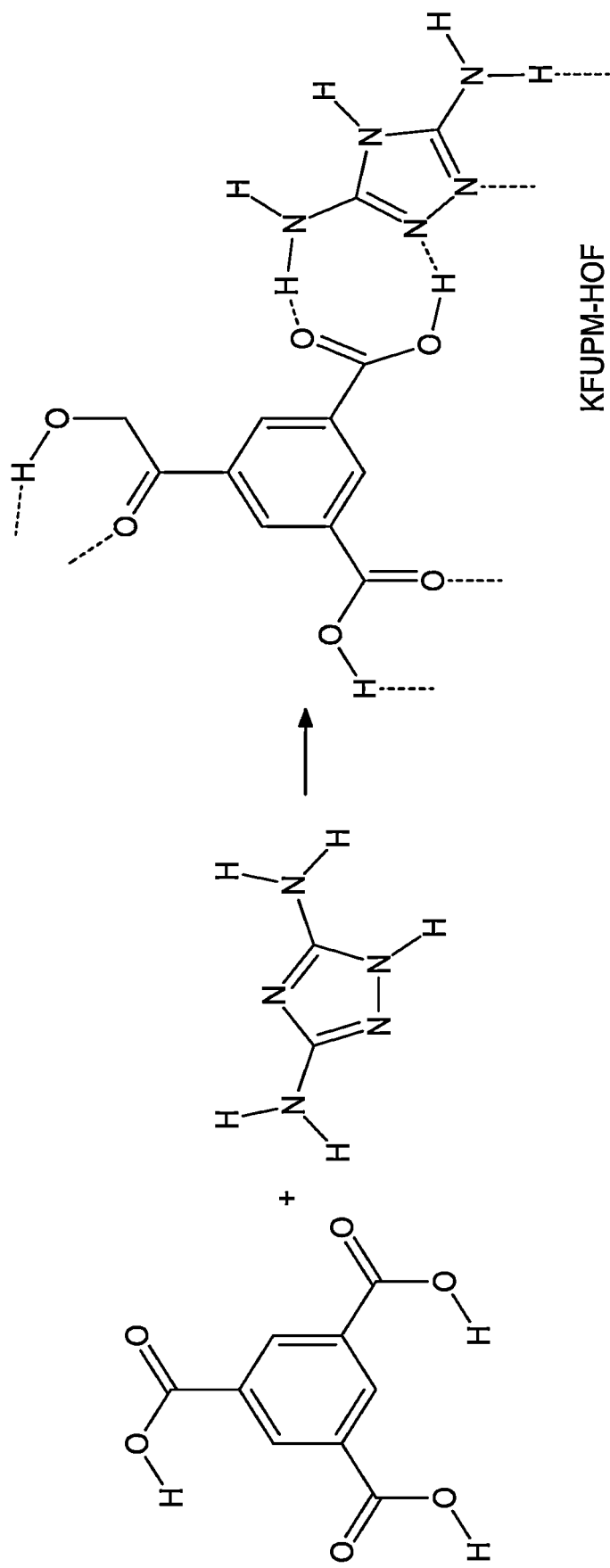
FIG. 1A shows a reaction diagram showing a synthesis of KFUPM-HOF, in which trimesic acid (TMA) reacts with guanazole (GZ), according to certain embodiments.

The definitions of the terms as used herein are as follows. Unless specified otherwise, these terms are used alone or in combination with another term in the meaning as defined.

The term "organic linker" means a chemical compound having a chemical structure substituted with (a) at least one functional group, wherein the said functional group is capable of promoting hydrogen bond(s) with at least one other organic linker.

The term "hydrogen bond" means a bond that results from an attractive interaction between a hydrogen atom and an electronegative atom, wherein the hydrogen atom itself is covalently attached to another electronegative atom, for example, but not limited to, oxygen (O), nitrogen (N), chlorine (Cl), fluorine (F), etc.

The term "hydrogen-bonded organic framework" or "HOF" is defined as a material assembled from organic linker molecules through intermolecular hydrogen bonding.

The term "one-pot" reaction or method is defined as a process where a compound is subjected to one or more reactions or interactions in a single vessel. In the case of the current disclosure, the compound is trimesic acid, which interacts with the aromatic compound to form the HOF in a single vessel.

The term "aliphatic compounds" or "acyclic compounds" means hydrocarbons characterized by open, straight, or branched, saturated or unsaturated, substituted or unsubstituted chains, typically having between 1 and 22 carbon atoms. Non-limiting examples of saturated, substituted or unsubstituted aliphatic groups include methane, ethane, n-propane, n-butane, t-butane, isobutane, sec-butane, n-pentane, n-hexane, n-heptane, n-octane, and the higher homologs and isomers. Non-limiting examples of unsaturated, substituted or unsubstituted aliphatic groups having one or more double or triple bonds include ethene, propene, 1-butene, 2-butene, isobutylene, 1-pentene, 2-pentene, 2-methyl-1-butene, 3-methyl-1-butene, 2-methyl-2-butene, ethyne, 1- and 3-propyne, 3-butyne, and the higher homologs and isomers.

The term "cyclic compounds" means hydrocarbons characterized by closed, saturated or unsaturated, substituted or unsubstituted homocyclic or heterocyclic rings typically having between 3 and 9 atoms. The rings may exhibit aromatic or non-aromatic behavior.

The term "aromatic compounds" means hydrocarbon rings that, in accordance with the theory of Hückel, have a cyclic, delocalized (4n+2) pi-electron system. Non-limiting examples of aromatic compounds include benzene, benzene derivatives, compounds having at least one benzene ring in their chemical structure, toluene, ethylbenzene, p-xylene, m-xylene, mesitylene, durene, 2-phenylhexane, biphenyl, phenol, aniline, nitrobenzene, benzoic acid, aspirin, paracetamol, picric acid, naphthalene, fluorene, anthracene, phenanthrene, phenalene, tetracene, chrysene, triphenylene, pyrene, pentacene, perylene, benzo[a]pyrene, corannulene, benzo[ghi]perylene, coronene, ovalene, benzo[c]fluorene, porphyrins, porphin, octaethylporphyrin, tetraphenylporphyrin, protoporyrin ix, and the like.

The term "non-aromatic compounds" includes cyclic hydrocarbons that do not exhibit aromatic behavior.

The term "carbocyclic compounds" includes cyclic hydrocarbons characterized by substituted or unsubstituted, saturated or unsaturated, aromatic or non-aromatic, hydrocarbon ring having 3 to 9 carbon atoms. Non-limiting examples of saturated or unsaturated, substituted or unsubstituted homocyclic rings include cyclopropane, cyclobutane, cyclopentane, cyclohexane, 1-cyclohexane, 3-cyclohexane, cycloheptane, and the higher homologs and isomers.

The term "heterocyclic compounds" includes cyclic hydrocarbons characterized by substituted or unsubstituted, saturated or unsaturated, aromatic or non-aromatic, hydrocarbon ring having 3 to 9 carbon atoms, wherein one or more of the atoms in the ring is an element other than carbon, for example, but not limited to, nitrogen, sulfur, or oxygen. Non-limiting examples of saturated or unsaturated, substituted or unsubstituted heterocyclic rings include pyrrolidine, 3-pyrroline, 2-pyrroline, 2H-pyrrole, 1H-pyrrole, pyrazolidine, imidazolidine, 2-pyrazoline, 2-imidazoline, pyrazole, imidazole, 1,24-triazole, 1,2,3-triazole, tetrazole, piperidine, pyridine, piperazine, pyridazine, pyrimidine, pyrazine, 1,2,4-triazine, 1,3,5-triazine, morpholine, 4H-1,2-oxazine, 2H-1,2-oxazine, 6H-1,2-oxazine, 4H-1,3-oxazine, 2H-1,3-oxazine, 6H-1,3-oxazine, 4H-1,4-oxazine, 2H-1,4-oxazine, thiomorpholine, 4H-1,4-thiazine, 2H-1,2-thiazine, 6H-1,2-thiazine, 2H-1,4-thiazine, cytosine, thymine, uracil, thiomorpholine dioxide, 2,3-dihydroazepine, 2,5-dihydroazepine, 4,5-dihydroazepine, azepine, 2H-azepine, 3H-azepine, 4H-azepine, 1,2-diazepine, 1,3-diazepine, 1,4-diazepine, azocane, azocine, oxazole, isoxazole, isothiazole, thiazole, 1,2-oxathiolane, 1,3-oxathiolane, 1,2,5-oxadiazole, 1,2,3-oxadiazole, 1,3,4-thiadiazole, 1,2,5-thiadiazole, sulfolane, 2,4-thiazolidinedione, succinimide, 2-oxazolidine, hydantoin, tetrahydrofuran, furan, 1,3-dioxolane, tetrahydrothiophene, thiophene, tetrahydropyran, 2H-pyran, 4H-pyran, pyrylium, 1,4-dioxane, 1,4-dioxine, thiane, 2H-thiopyran, 4H-thiopyran, 1,3-dithiane, 1,4-dithiane, 1,3,5-trithiane, oxepane, thiepine, 1,4-thiazepine and the like.

The term "aromatic carbocyclic compounds" includes cyclic hydrocarbons characterized by substituted or unsubstituted, unsaturated, aromatic, hydrocarbon ring having 3 to 9 carbon atoms.

The term "non-aromatic carbocyclic compounds" includes cyclic hydrocarbons characterized by substituted or unsubstituted, saturated or unsaturated, non-aromatic hydrocarbon ring having 3 to 9 carbon atoms.

The term "aromatic heterocyclic compounds" includes cyclic hydrocarbons characterized by substituted or unsubstituted, unsaturated, aromatic, hydrocarbon ring having 3 to 9 carbon atoms, wherein one or more of the atoms in the ring is an element other than carbon, for example, but not limited to, nitrogen, sulfur, or oxygen.

The term "non-aromatic heterocyclic compounds" includes cyclic hydrocarbons characterized by substituted or unsubstituted, saturated or unsaturated, non-aromatic, hydrocarbon ring having 3 to 9 carbon atoms, wherein one or more of the atoms in the ring is an element other than carbon, for example, but not limited to, nitrogen, sulfur, or oxygen.

The term "amines", "amine compounds", or "amine substituted compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) at least one functional group of formula —$NR_aR_b$, or (b) at least one moiety having at least one functional group of formula —$NR_aR_b$, wherein $R_a$ and $R_b$ are each independently hydrogen, alkyl, aryl, heterocyclyl, or any other substituent. Non-limiting examples of amines include aminobenzene, 3-amino-1,2,4-triazole, 5-amino-1,2,4-triazole, 4-amino-1,2,3-triazole, 5-amino-1,2,3-triazole, 5-aminotetrazole, 2-amino-1,3,5-triazine, 3-amino-1,2,4-triazine, 5-amino-1,2,4-triazine, 6-amino-1,2,4-triazine, and like.

The term "di-amines" or "di-amine compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) two functional groups of formula —$NR_aR_b$, (b) a moiety having two functional groups of formula —$NR_aR_b$, or (c) two same or different moieties, each substituted with a functional group of formula —$NR_aR_b$, wherein $R_a$ and $R_b$ are each independently hydrogen, alkyl, aryl, heterocyclyl, or any other substituent. Non-limiting examples of di-amines include p-Phenylenediamine, o-Phenylenediamine, m-Phenylenediamine, Dimethyl-4-phenylenediamine, N,N,N',N'-tetramethyl-p-phenylenediamine, N,N-diethyl-p-phenylenediamine, 4-N,4-N-diethyl-2-methylbenzene-1,4-diamine, 3,5-diamino-1,2,4-triazole, 4,5-diamino-1,2,3-triazole, and the like.

The term "tri-amines" or "tri-amine compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) three functional groups of formula —$NR_aR_b$, (b) a moiety having three functional groups of formula $NR_aR_b$, or (c) three same or different moieties, each substituted with a functional group of formula —$NR_aR_b$, wherein $R_a$ and $R_b$ are each independently hydrogen, alkyl, aryl, heterocyclyl, or any other substituent. Non-limiting examples of tri-amines include benzene-1,2,3-triamine, benzene-1,2,4-triamine, benzene-1,3,5-triamine, 2,4,6-triamino-1,3,5-triazine, 3,5,6-triamino-1,2,4-triazine, and the like.

The term "carboxylic acids" or "carboxylic acid compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) at least one functional group of formula —COH, or (b) at least one moiety having at least one functional group of formula —COOH. Non-limiting examples of di-carboxylic acids include benzoic acid, 3-carboxy-1,2,4-triazole, 5-carboxy-1,2,4-triazole, 4-carboxy-1,2,3-triazole, 5-carboxy-1,2,3-triazole, 5-carboxytetrazole, 2-carboxy-1,3,5-triazine, 3-carboxy-1,2,4-triazine, 5-carboxy-1,2,4-triazine, 6-carboxy-1,2,4-triazine, and like.

The term "di-carboxylic acids" or "di-carboxylic compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) two functional groups of formula —COOH, (b) a moiety having two functional groups of formula —COOH, or (c) two same or different moieties, each substituted with a functional group of formula —COOH. Non-limiting examples of di-carboxylic acids include Phthalic acid, Isophthalic acid, Terephthalic acid, 2,4-pyrrolidinedicarboxylic acid, 3,5-dicarboxy-1,2,4-triazine, 3,5-dicarboxy-1,2,4-triazole, diphenic acid, 2,6-naphthalenedicarboxylic acid, and the like.

The term "tri-carboxylic acids" or "tri-carboxylic compounds" includes aliphatic, cyclic, aromatic, non-aromatic, carbocyclic, heterocyclic, aromatic carbocyclic, non-aromatic carbocyclic, aromatic heterocyclic, or non-aromatic heterocyclic hydrocarbons that are substituted with (a) three functional groups of formula —COOH, (b) a moiety having three functional groups of formula —COOH, or (c) three same or different moieties, each substituted with a functional group of formula —COOH. Non-limiting examples of carboxylic acids include trimesic acid, trimellitic acid, hemimellitic acid, 2,4,6-tricarboxy-1,3,5-triazine, 3,5,6-tricarboxy-1,2,4-triazine, and the like.

The term "organic solvent" refers to carbon-based substances capable of dissolving or dispersing one or more other substances, which includes but is not limited to acetone, acetonitrile, ethanol, formaldehyde, ether, ethyl acetate, hexane, toluene, xylenes, methylene chloride, and chloroform.

In the drawings, like reference numerals designate identical or corresponding parts throughout the several views. As used herein, the words "a," "an" and the like generally carry a meaning of "one or more," unless stated otherwise. Further, the terms "approximately," "approximate," "about," and similar terms generally refer to ranges that include the identified value within a margin of 25%, 20%, 10%, or 5%, and any values therebetween. Furthermore, the terms "equal to," "substantially equal to," and similar terms generally refer to ranges that include the identified value within a margin of 75%, 80%, 85%, 90%, 95%, or 100%, and any values therebetween.

Aspects of the present disclosure are directed towards a simple one-pot green synthesis of hydrogen-bonded organic frameworks (HOFs). The synthesis method can be generalized and applied for making a variety of HOFs using water soluble organic linkers. The mechanism of self-assembly of HOFs via intermolecular hydrogen-bonding interactions between the organic linkers is illustrated. Further, the present disclosure is directed towards the synthesis of HOFs using only water as a solvent for carrying out the synthesis reaction. Furthermore, the disclosed method of synthesis employs no additional reagent or catalyst to make the HOFs of the present disclosure.

In one aspect of the present disclosure, the method utilizes di- or tri-amine compounds as organic linkers to yield the HOFs. The di- or tri-amines utilized may be di- or tri-amine-substituted acyclic or cyclic compounds. Any type of acyclic compounds is contemplated herein, for example, but not limited to, open-chain, straight-chain, or branched-chain compounds. The said compounds may be saturated or unsaturated acyclic compounds. Further, any type of cyclic compounds is contemplated herein, comprising one or more rings. The cyclic compounds may be 3-, 4-, 5-, 6-, 7-, 8-, or 9-membered ring compounds of any type, for example, but not limited to, non-aromatic carbocyclic, aromatic carbocyclic, non-aromatic heterocyclic, or aromatic heterocyclic ring compounds. The said rings may be fused/condensed rings of any of the aforementioned type, or a combination thereof.

In another aspect of the present disclosure, the method utilizes di- or tri-carboxylic acid compounds as organic linkers to yield the HOFs. The di- or tri-carboxylic acids utilized may be di- or tri-carboxylic acid substituted acyclic or cyclic compounds. Any type of acyclic compounds is contemplated herein, for example, but not limited to, open-chain, straight-chain, or branched-chain compounds. The said compounds may be saturated or unsaturated acyclic compounds. Further, any type of cyclic compounds is contemplated herein comprising one or more rings. The cyclic compounds may be 3-, 4-, 5-, 6-, 7-, 8-, or 9-membered ring compounds of any type, for example, but not limited to, non-aromatic carbocyclic, aromatic carbocyclic, non-aromatic heterocyclic, or aromatic heterocyclic ring compounds. The said rings may be fused/condensed rings of any of the aforementioned type, or a combination thereof.

In another aspect of the present disclosure, the method disclosed employs di- or tri-amine compounds and di- or tri-carboxylic acid compounds as organic linkers, wherein said linkers interact with one another and form hydrogen bonds, thus creating a framework comprising a multitude of interconnections forming a porous scaffold known as HOF. In some examples, the method uses aromatic di- or tri-amines and di- or tri-carboxylic acids as organic linkers. In some examples, the method uses aromatic di- or tri-amines and tri-carboxylic acids as organic linkers.

The HOFs, according to the present disclosure, may comprise a single type of organic linker or two different types of organic linkers. It is contemplated that the hydrogen bond formation promoting functional group(s) attached directly or indirectly to the chemical structure of one type of organic linker, may interact with other organic linkers of same type and create intermolecular H-bonds. It is also contemplated that the hydrogen bond formation promoting functional group(s) attached directly or indirectly to the chemical structure of one type of organic linker, may interact with other organic linkers of different type and create intermolecular H-bonds. It is further contemplated that the hydrogen bond formation promoting functional group(s) attached directly or indirectly to the chemical structure of one type of organic linker, may interact with electronegative atoms (if any) present in the chemical structures of other organic linkers of same or different type and create intermolecular H-bonds.

The method of synthesis of HOFs are described in more detail. In one aspect of the present disclosure, the method of making HOF includes dissolving a carboxylic acid compound in water to form a first solution. The first solution may be formed by dissolving a di- or tri-carboxylic acid of any kind in water. In a non-limiting example, the dicarboxylic acid may be selected from a group consisting of phthalic acid, isophthalic acid, terephthalic acid, diphenic acid, 2,6-naphthalenedicarboxylic acid, fumaric acid, polyacrylic acid, or any other dicarboxylic acid. In a non-limiting example, the tricarboxylic acid may be selected from a group consisting of citric acid, isocitric acid, aconitic acid, propane-1,2,3-tricarboxylic acid, agaric acid, trimesic acid, trimellitic acid, hemimellitic acid, or any other tricarboxylic acid. In one aspect of the present disclosure, the tricarboxylic acid is trimesic acid.

The step of dissolution of carboxylic acids in water to form a first solution is carried out at an elevated temperature compared to the standard ambient temperature (i.e. 25° C.). In a non-limiting example, the elevated dissolution temperature is at least 5° C., 10° C., 15° C., 20° C., 25° C., 30° C., 35° C., 40° C., or 45° C. higher than the standard ambient temperature. In some examples, the elevated dissolution temperature is at least 35° C., 40° C., or 45° C. higher than the standard ambient temperature. In some examples, the temperature is slowly increased at least till 60° C., 65° C., or 70° C. while stirring until complete dissolution of the carboxylic acid is achieved.

The method includes dissolving an amine substituted compound in water to form a second solution. The second solution may be prepared by dissolving a di- or tri-amine compound in water. The di- or tri-amine compound may be an aromatic, a heterocyclic, a non-aromatic heterocyclic, an aromatic heterocyclic compound, or any other kind, as discussed earlier. In an aspect of the present disclosure, the di- or tri-amine compound is an aromatic compound selected from a group consisting of guanazole, melamine, or p-phenylenediamine.

The amine substituted compound and the carboxylic acid compound in the first and the second solution, respectively, may be present in any concentration. In a non-limiting example, the concentration of the first and the second solution can be selected, independently, from a range from about 0.01 M to about 100 M, from about 0.5 M to about 75 M, from about 0.25 M to about 50 M, from about 0.1 M to about 25 M, from about 1 M to about 10 M, or from about 5 M to 10 M.

The second solution is added into the first solution to form a synthetic solution. Adding the second solution to the first solution and the second is carried out at an elevated temperature compared to the standard ambient temperature. In a non-limiting example, the elevated dissolution temperature is at least 5° C., 10° C., 15° C., 20° C., 25° C., 30° C., 35° C., 40° C., or 45° C. higher than the standard ambient temperature. The elevated dissolution temperature may be at least 35° C. higher than the standard ambient temperature. In an example, the addition of the second solution into the first solution to form the synthetic solution is performed in a dropwise manner. Furthermore, in an aspect of the present disclosure, the temperature of the first solution during the dropwise addition of the second solution does not vary by more than 5° C., preferably 3° C., or 1° C. Additionally, the first solution during the dropwise addition of the second solution, is stirred, preferably in a continuous manner, at a rate of 600-800 RPM, preferably 650-750 RPM, or 700-725 RPM. In some examples, the addition of the second solution into the first solution to form the synthetic solution is performed rapidly i.e., the second solution is poured in all in one step without dropwise addition.

In some embodiments, the amine substituted compound and carboxylic acid compound may be mixed in any stoichiometric ratio. In a non-limiting example, the amine substituted compound and carboxylic acid compound may be mixed in a molar ratio such that the amine substituted compound is at least 10 times, at least 9 times, at least 8 times, at least 7 times, at least 6 times, at least 5 times, at least 4 times, at least 3 times, or at least 2 times the carboxylic acid compound. In another non-limiting example, the amine substituted compound and carboxylic acid compound may be mixed in a molar ratio such that the carboxylic acid compound is at least 10 times, at least 9 times, at least 8 times, at least 7 times, at least 6 times, at least 5 times, at least 4 times, at least 3 times, or at least 2 times the amine substituted compound. In another non-limiting example, the amine substituted compound and carboxylic acid compound may be mixed in a 1:1 molar ratio.

Then, the synthetic solution is cooled to form precipitate. The cooling requires the synthetic solution to be at least below 60° C. to form the precipitate. In some examples, the solution is cooled below 50° C. to form the precipitate. In some examples, the solution is cooled below 40° C. to form the precipitate. The cooling of the solution may be achieved through any known passive or active cooling methods. In some examples, the solution is cooled naturally by dissipation of heat from the solution in ambient conditions.

The precipitate may be separated and dried to yield the HOF. Separating and drying the precipitate involves the separation of the precipitate from the solution by any of the known methods, for example, but not limited to, gravity filtration, vacuum filtration, centrifugal filtration, mechanical filtration, or decanting. The drying of filtrate is carried out at an elevated temperature of, for example, but not limited to, at least 50° C., at least 55° C., at least 60° C., or at least 65° C. In an example, the drying is performed at temperature of at least 60° C. In some examples, the drying may be carried out in a vacuum oven.

Figure 1B:
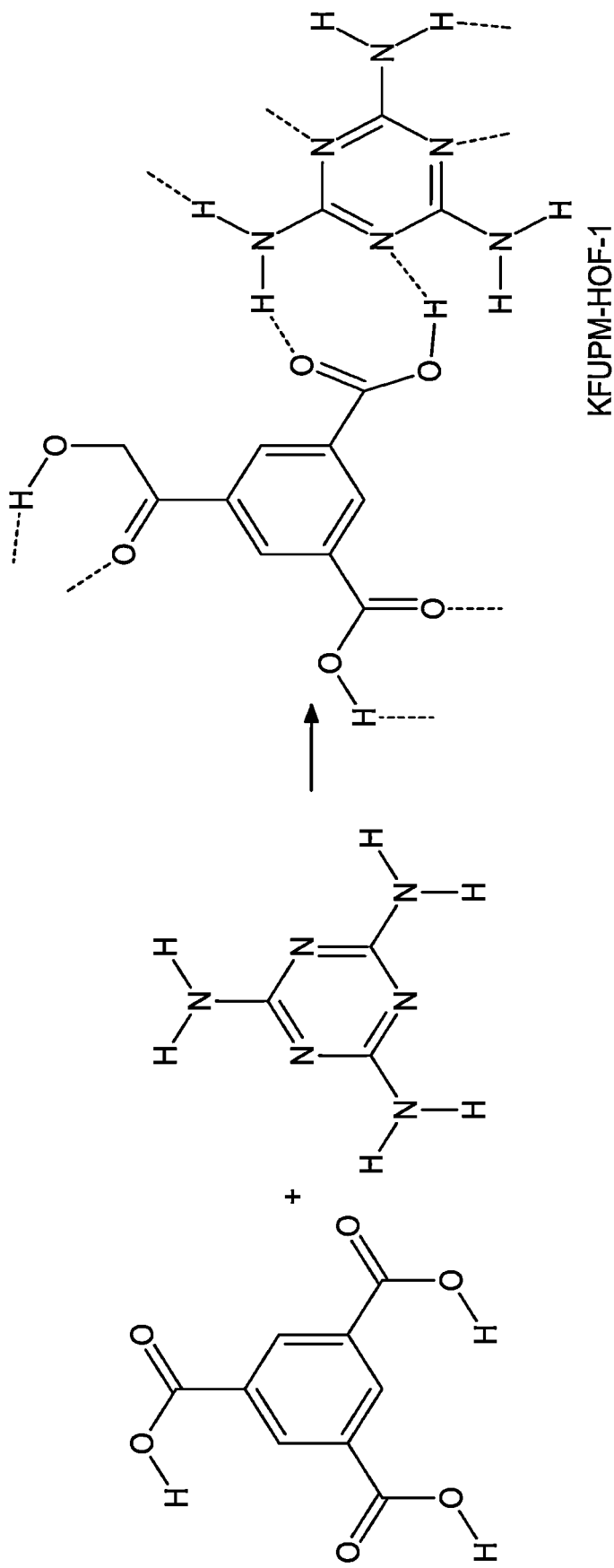
FIG. 1B shows a reaction diagram showing a synthesis of KFUPM-HOF-1, in which trimesic acid (TMA) reacts with melamine (MA), according to certain embodiments.
Figure 1C:
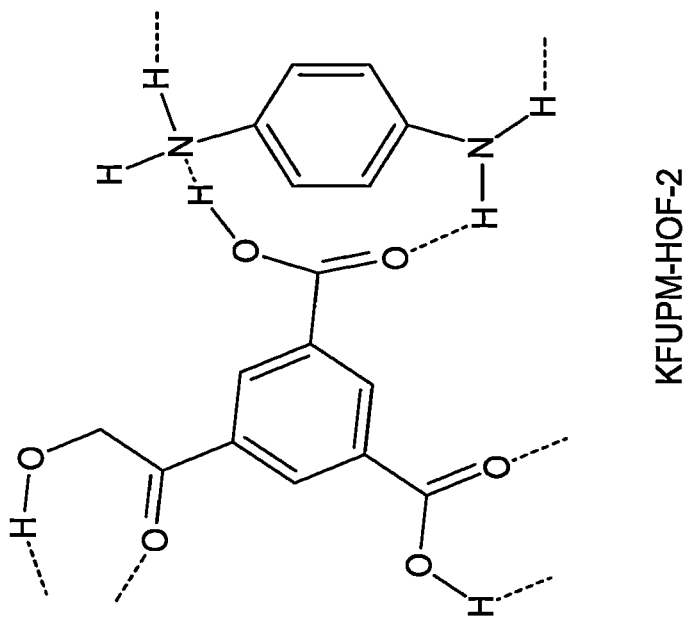
FIG. 1C shows a reaction diagram showing a synthesis of KFUPM-HOF-2, in which trimesic acid (TMA) reacts with p-Phenylenediamine (p-PD), according to certain embodiments.
Figure 1C:
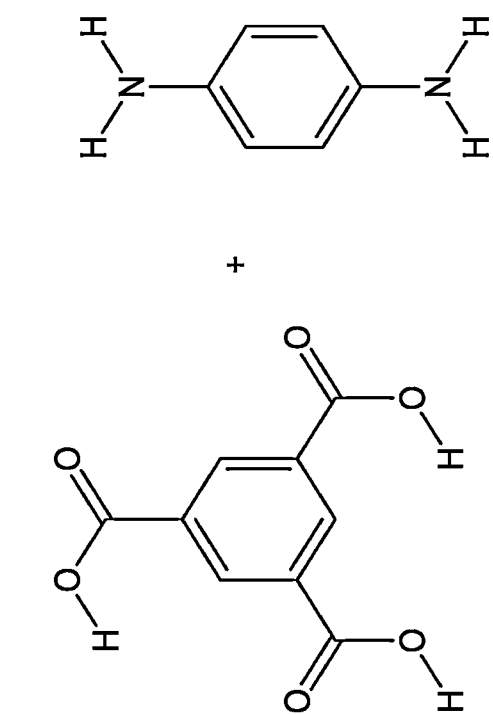

In one aspect of the present invention, the method of making a HOF in an aqueous environment is carried out in accordance with FIG. 1A-1C. FIG. A-IC utilizes a tricarboxylic acid compound of formula I and a di-amine compound of formula II or III to yield an HOF. The compound of formula I is defined below:

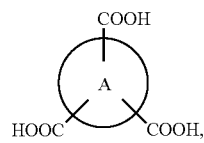

[Formula I]

where: the ring A represents a 5- or 6-membered carbocyclic ring or a 5- or 6-membered heterocyclic ring. In a non-limiting example, the 5- or 6-membered heterocyclic ring may be selected from a group consisting of the formulas from Formula I-a to Formula I-h:

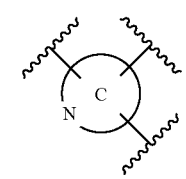

[Formula I-a]

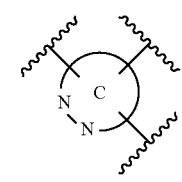

[Formula I-b]

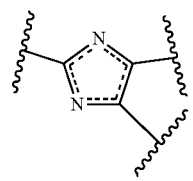

[Formula I-c]

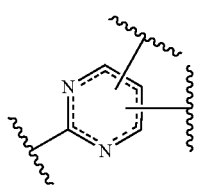

[Formula I-d]

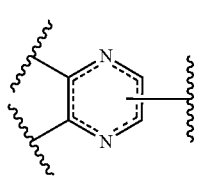

[Formula I-e]

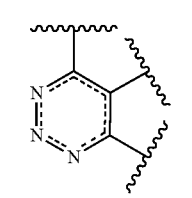

[Formula I-f]

-continued

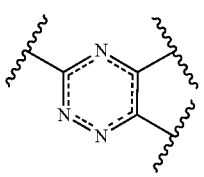
[Formula I-g]

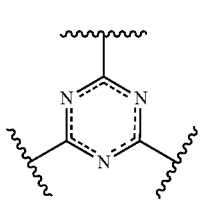
[Formula I-h]

where: the wavy line (∼) indicates the point of attachment to the carboxy groups of the formula I, the dashed lines (═) in any of the formulae from formula I-a to formula I-h represent single or double bonds; and, the ring C together with nitrogen (N) atom(s) form(s) a non-aromatic or an aromatic hydrocarbon ring in formula II-a and formula II-b.

In a non-limiting example, the ring C of formula I-a may be selected from a pyrrolidine derivative, a pyrroline derivative, a pyrrole derivative, a piperidine derivative, or a pyridine derivative. In a non-limiting example, the ring C of formula I-b may be selected from a pyrazolidine derivative, a pyrazoline derivative, a pyrazole derivative, a pyridazine derivative. Further, it is contemplated that one or more N hetero atoms in formulae I-a to I-h may be replaced by any other suitable heteroatom, for example, but not limited to, oxygen (O), and sulfur (S).

The compound of formula II is defined below:

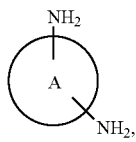
[Formula II]

where: the ring A represents a 5- or 6-membered carbocyclic ring or a 5- or 6-membered heterocyclic ring. In a non-limiting example, the 5- or 6-membered heterocyclic ring may be selected from a group consisting of formulae from formula II-a to formula II-k:

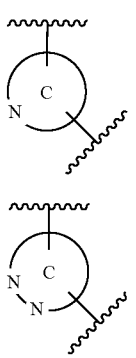
[Formula II-a]

[Formula II-b]

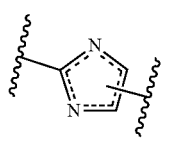
[Formula II-c]

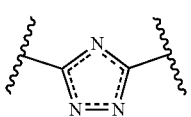
[Formula II-d]

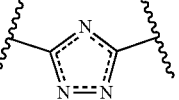
[Formula II-e]

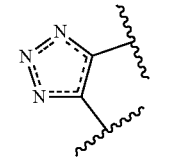
[Formula II-f]

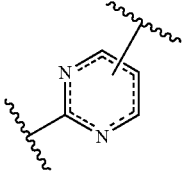
[Formula II-g]

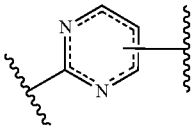
[Formula II-h]

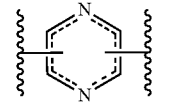
[Formula II-i]

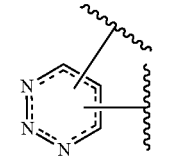
[Formula II-j]

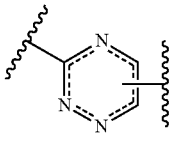
[Formula II-k]

where: the wavy line (∼) indicates the point of attachment to the amino groups of the formula II, the dashed lines (═) in any of the formulae from formula II-a to formula II-k represent single or double bonds, and, the ring C together with N atom forms a non-aromatic or aromatic hydrocarbon ring in formula II-a and formula II-b.

In a non-limiting example, the ring C of formula II-a may be selected from a pyrrolidine derivative, a pyrroline derivative, a pyrrole derivative, a piperidine derivative, or a pyridine derivative. In a non-limiting example, the ring C of formula II-b may be selected from a pyrazolidine derivative, a pyrazoline derivative, a pyrazole derivative, a pyridazine derivative. Further, it is contemplated that one or more N hetero atoms in formulae II-a to II-k may be replaced by any other suitable heteroatom, for example, but not limited to, O, and S.

The method in FIG. 1A, exhibits an exemplary HOF, synthesized with the tricarboxylic acid compound of formula I and the di-amine compound of formula II. In an embodiment, the tricarboxylic acid compound is trimesic acid and the di-amine is guanazole to generate KFUPM-HOF. FIG. 1A yields a HOF product having a macroporous network of intercrossed sheet structures with pores on the surface. The sheet structures may have a thickness ranging from 3-100 nm, preferably 10-90 nm, 20-80 nm, 30-70 nm, 40-60 nm or approximately 50 nm. Further, the pores of the resulting HOF may have a diameter ranging from 300-800 nm, preferably 350-750 nm, 400-700 nm, 450-650 nm, 500-600 nm, or approximately 550 nm. Furthermore, the synthesized HOF may exhibit stability up to 320° C., preferably 250-320° C., or 275-300° C.

The method in FIG. 1B, exhibits another exemplary HOF, also synthesized with the tricarboxylic acid compound of formula I and the di-amine compound of formula II. In an embodiment, the tricarboxylic acid compound is trimesic acid and the di-amine is melamine to generate KFUPM-HOF-1. FIG. 1B yields a HOF product having a rod morphology, wherein the rods may comprise fused sheets or sheet-like structures. The rods may have a length of 0.5-4 μm, preferably 1-3.5 μm, 1.5-3 μm, or 2-2.5 μm and a width of 200-600 nm, preferably 250-550 nm, 300-500 nm, 350-450 nm, or approximately 400 nm. The synthesized HOF may exhibit stability up to 260° C., preferably 200-260° C., or 230-240° C.

The method in FIG. 1C, exhibits yet another exemplary HOF, synthesized with the tricarboxylic acid compound of formula I and the di-amine compound of formula III (below). In an embodiment, the tricarboxylic acid compound is trimesic acid and the di-amine is p-phenylenediamine to generate KFUPM-HOF-2. FIG. 1B yields a HOF product having a sheet structure, wherein the sheets form a flower morphology. The sheets may have a thickness of 25-40 nm, preferably 28-38 nm, or 30-35 nm and the flowers may have a diameter of 1-5 μm, preferably 1.5-4.5 μm, 2-4 μm, 2.5-3.5 μm, or approximately 3 μm. The synthesized HOF may exhibit stability up to 280° C., preferably 200-280° C., or 220-250° C.

The compound of formula III is defined below:

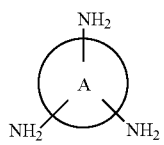

[Formula III]

where: the ring A represents a 5- or 6-membered carbocyclic ring or a 5- or 6-membered heterocyclic ring. In a non-limiting example, the 5- or 6-membered heterocyclic ring may be selected from a group consisting of formulae from formula III-a to formula III-h:

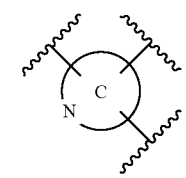

[Formula III-a]

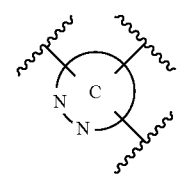

[Formula III-b]

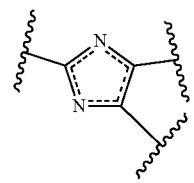

[Formula III-c]

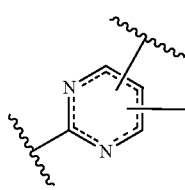

[Formula III-d]

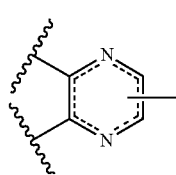

[Formula III-e]

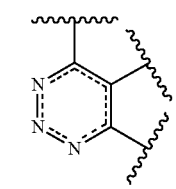

[Formula III-f]

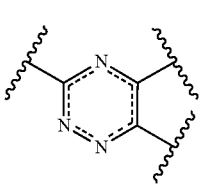

[Formula III-g]

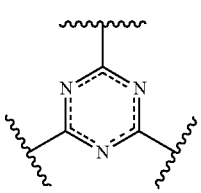

[Formula III-h]

where: the wavy line (∼) indicates the point of attachment to the amino groups of the formula III, the dashed lines (═) in any of the formulae from formula II-a to formula II-k represent single or double bonds, and, the ring C together with Nitrogen (N) atom forms a non-aromatic or aromatic hydrocarbon ring in formula III-a and formula III-b.

In a non-limiting example, the ring C of formula III-a may be selected from a pyrrolidine derivative, a pyrroline derivative, a pyrrole derivative, a piperidine derivative, or a pyridine derivative. In a non-limiting example, the ring C of formula III-b may be selected from a pyrazolidine derivative, a pyrazoline derivative, a pyrazole derivative, a pyridazine derivative. Further, it is contemplated that one or more N hetero atoms in formulae I-a to I-h may be replaced by any other suitable heteroatom, for example, but not limited to, O and S.

Figure 2A:
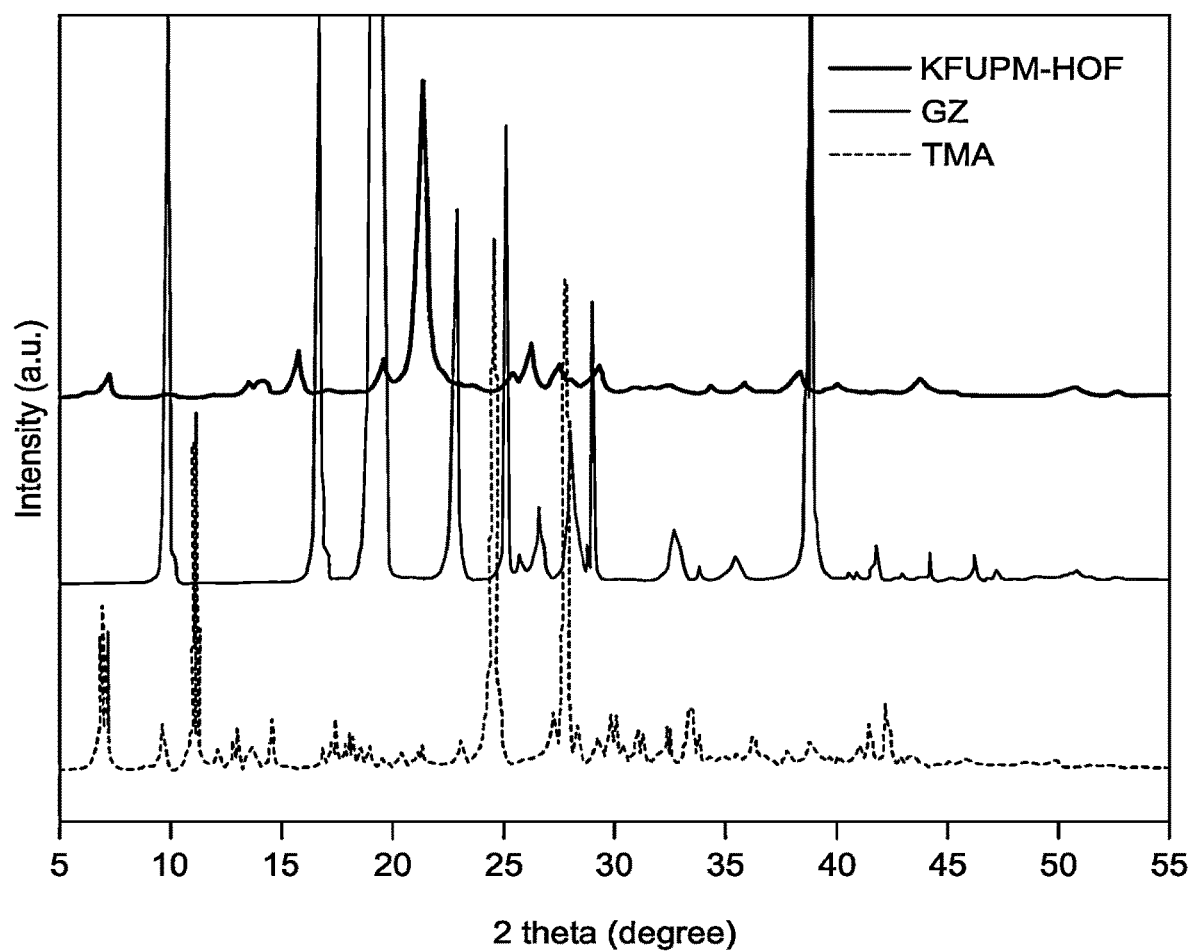
FIG. 2A shows PXRD plot depicting a spectrum of TMA, GZ, and KFUPM-HOF, according to certain embodiments.
Figure 2B:
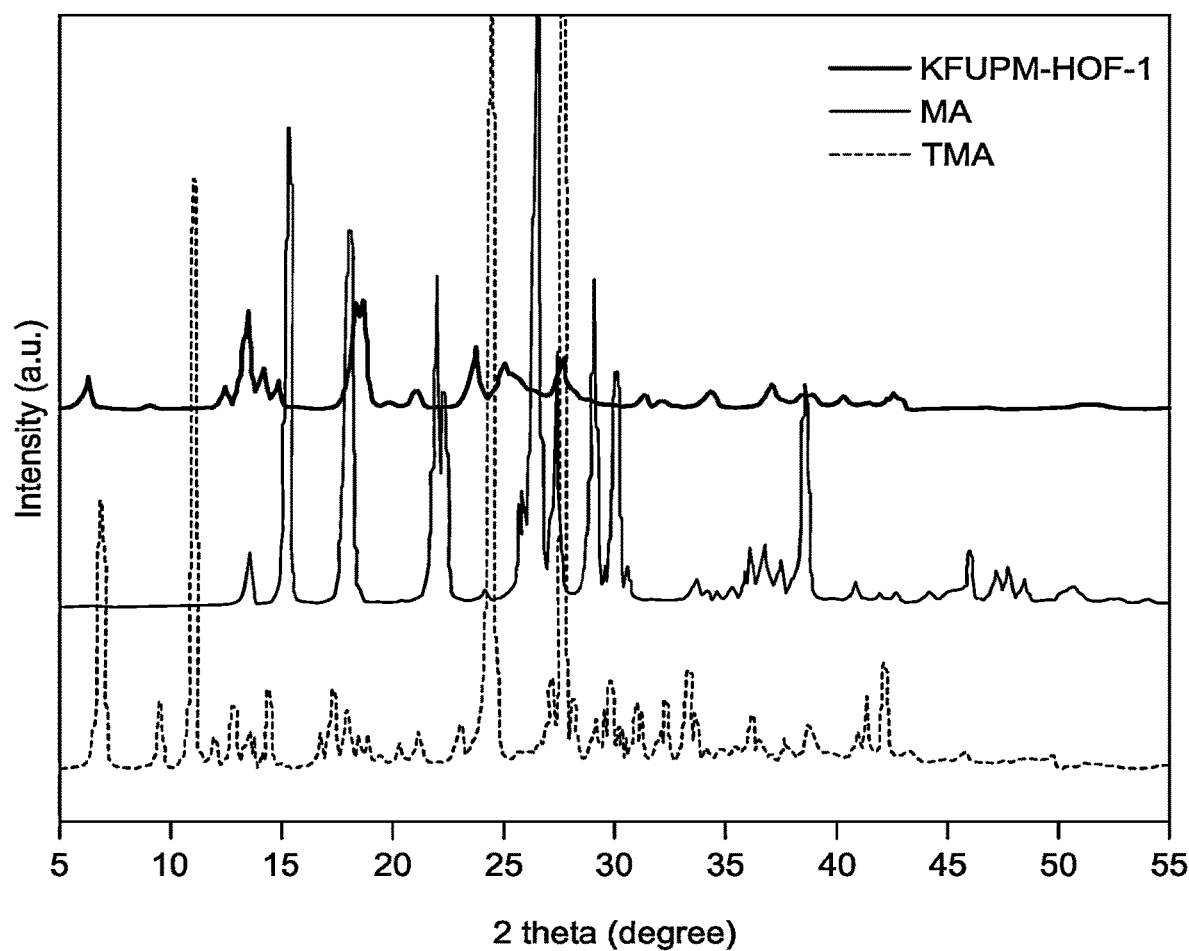
FIG. 2B shows PXRD plot depicting a spectrum of TMA, MA, and KFUPM-HOF-1, according to certain embodiments.
Figure 2C:
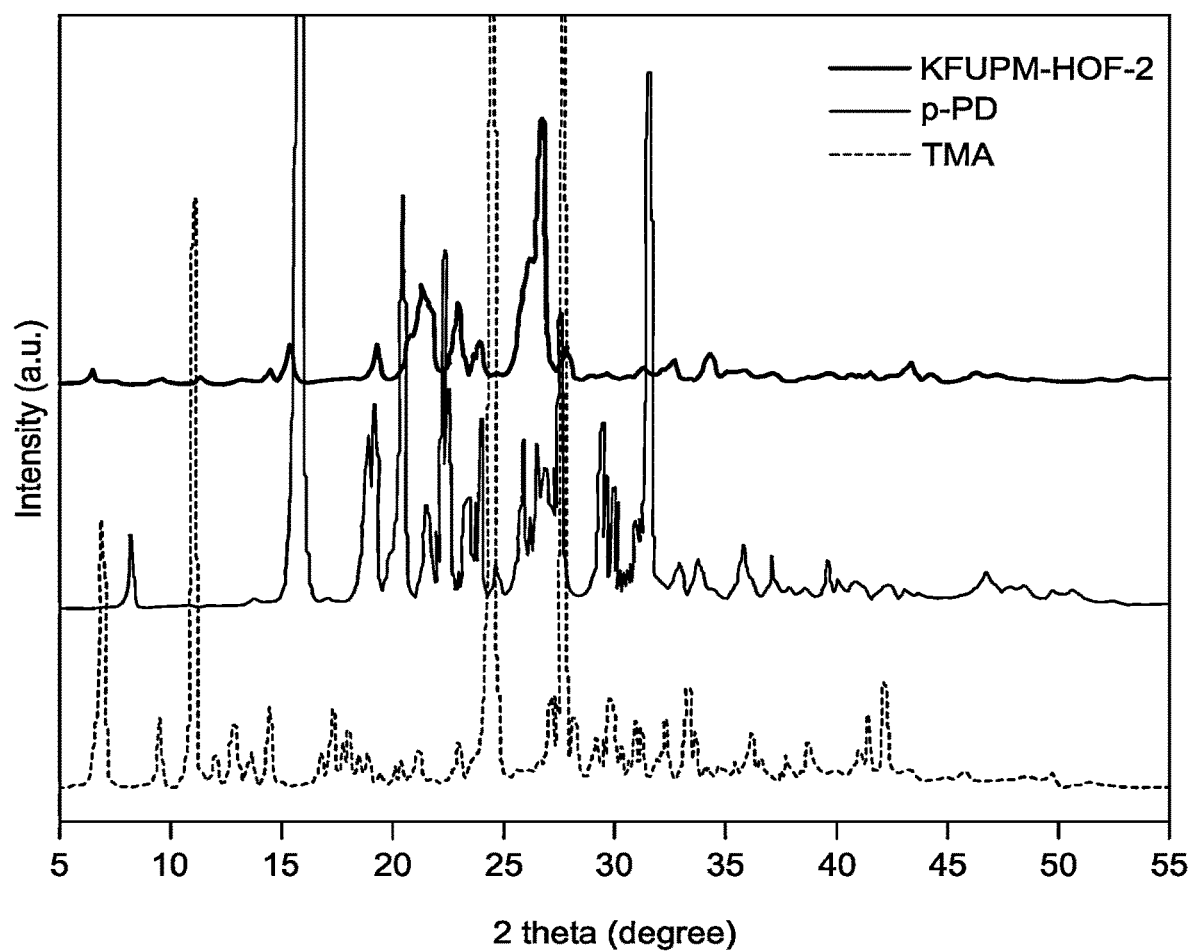
FIG. 2C shows PXRD plot depicting a spectrum of TMA, p-PD, and KFUPM-HOF-2, according to certain embodiments.

The HOF obtained by the method of the present disclosure yields a substantially crystalline HOF, based on the PXRD profiles FIG. 2A-2C. In some embodiments, the HOF is at least 50% crystalline, preferably 60%, 70%, 80%, 90%, or 100% crystalline. The KFUPM-HOF synthesized with trimesic acid and guanazole, exhibits a peak at 6.5-8°, preferably 6.8-7.8°, or 7-7.5°, a peak at 15-16.5°, preferably 15.5-16.2°, or 15.7-16°, a peak at 18.5-21°, preferably 19-20.5°, or 19.5-20°, a peak at 20-22.5°, preferably 20.5-22°, or 21-21.5°, a peak at 25-27°, preferably 25.5-26.5°, or 26-26.2°, a peak at 27-28°, preferably 27.2-27.8°, or 27.4-27.6°, a peak at 28-30°, preferably 28.5-29.5°, or 29-29.2°, a peak at 37-39°, preferably 37.5-38.5°, or 38-38.2° and 43-45°, preferably 43.5-44.5°, and 44-44.3°. In case of KFUPM-HOF-1 synthesized with trimesic acid and melamine, a peak was located at 5-7°, preferably 5.5-6.5°, or 6-6.3°, a peak at 12.5-14.5,° preferably 13-14°, or 13.3-13.6°, a peak at 17.5-19.5°, preferably 18-19°, or 18.3-18.6°, a peak at 18-20°, preferably 18.2-19.5°, or 18.5-19°, a peak at 23-25°, preferably 23.5-24.5°, 23.7-24°, and a peak at 26.5-28.5°, preferably 27-28°, or 27.3-27.6°. The spectra of KFUPM-HOF-2 synthesized with trimesic acid and p-phenylenediamine, exhibits a peak at 14-17°, preferably 14.5-16.5°, or 15-15.5°, a peak at 18-20°, preferably 18.5-19.5°, or 19-19.3°, a peak at 19-22°, preferably 19.5-21.5°, or 20-21°, a peak at 20-23°, preferably 20.5-22.5°, or 21-21.5°, a peak at 20-23°, preferably 21-22.5°, or 21.5-22°, a peak at 22.0-26°, preferably 23-25°, or 23.5-24.5°, a peak at 24-28°, preferably 25-27°, or 25.5-26.5°, and a peak at 26-29°, preferably 26.5-28.5°, or 27-28°.

In an aspect of the present disclosure, the HOF obtained is substantially pure and does not comprise any non-hydrogen-bonded amine substituted compound. In an embodiment, a portion of the aromatic compound is not hydrogen bonded to the carboxylic acid compound. In an embodiment, 1-10%, preferably 2-8%, or 3-5% of the aromatic compound is not hydrogen bonded.

In various aspects of the present disclosure, the tricarboxylic acid compound of formula I is, preferably, trimesic acid (TMA). It is believed that the characteristics of TMA are likely to play an important role in the construction and stabilization of HOFs. TMA itself tends to form a honeycomb (hexagon shaped) crystal lattice structure through intermolecular hydrogen bonding, wherein the three carboxylic acid groups on the aromatic ring each hydrogen bond with another carboxylic acid group on an adjacent TMA molecule [Feyter, Steven & De Schryver, Frans. (2003). Two-Dimensional Supramolecular Self-Assembly Probed by Scanning Tunneling Microscopy. Chemical Society reviews. 32. 139-50, incorporated herein by reference in its entirety]. The existence of aromatic ring in TMA provides rigidity in the construction of HOF structure, while the presence of 3 alternate carboxylic acid groups results in a stable and proper orientation of the HOF. Therefore, the TMA can easily form infinite two-dimensional (2D) hydrogen bonded networks with amines. In comparison to other aromatic and aliphatic acids, TMA forms much more stable and rigid HOF which results in the construction of 2D HOF.

EXAMPLES

The present disclosure is further described by the following examples. These are not intended to limit the scope of the disclosure but represent some preferred aspects of the present disclosure.

All chemicals and solvents used in the Examples described below were purchased from commercial sources and were used as received without further purification.

Example 1: Preparation of KFUPM-HOF

Referring to FIG. 1A, a reaction diagram is illustrated, according to an aspect of the present disclosure. In this reaction diagram, the aromatic compound is guanazole (GZ) which reacts with trimesic acid under aqueous conditions to yield KFUPM-HOF.

Trimesic acid (TMA, 95%) and Guanazole (3,5-Diamino-1,2,4-triazole, 98%) were purchased from Sigma-Aldrich. Deionized (DI) water with a resistivity of 18.3 was used to prepare all of the solutions. A generalized aqueous synthesis of KFUPM-HOF is depicted in FIG. 1A. In order to obtain the HOF, the molar ratio of TMA over GZ was set to 1:1. For a typical synthesis of KFUPM-HOF, an aqueous solution of TMA (6.0 mmol) was prepared by dissolving of TMA in a round bottom flask by adding TMA in Milli-Q water, or deionized water under stirring. The temperature was increased slowly to 70° C. while stirring until complete dissolution of TMA. The solution of GZ (6.0 mmol) was prepared separately in Milli-Q water. Both solutions were mixed by dropping solution of GZ to TMA while stirring continuously. After complete addition of GZ, the solution was removed from the hot plate and allowed to cool naturally. When the temperature of the solution reached around 40° C., the precipitation of a white solid was observed. The precipitate was filtered and dried at 65° C. in a vacuum oven. The yield of the KFUPM-HOF was found to be more than 95%.

Example 2: Preparation of KFUPM-HOF-1 and KFUPM-HOF-2

Referring to FIG. 1B and FIG. 1C, reaction diagrams are illustrated, according to other aspects of the present disclosure, to synthesize KFUPM-HOF-1 and KFUPM-HOF-2, respectively. The method described in example 1 was extended for preparation of KFUPM-HOF-1 and KFUPM-HOF-2. KFUPM-HOF-1, as shown in FIG. 1B, was prepared by reacting TMA with Melamine (MA, 99%, Sigma-Aldrich) in an aqueous environment. KFUPM-HOF-2, as shown in FIG. 1C, was prepared by reacting TMA with p-Phenylenediamine (p-PD, 98%, Sigma-Aldrich) in an aqueous environment.

Example 3: Characterization of HOFs

The synthesized HOFs were characterized with $^1$H NMR, $^{13}$C NMR and FTIR spectra. $^1$H and $^{13}$C NMR spectra were recorded on a Bruker AM-400 spectrometer using TMS (trimethylsilane) as the internal standard. The Fourier-Transform Infrared (FTIR) spectra were obtained using a Nicolet 6700 Thermo Scientific instrument in the range of 400-4000 cm$^{-1}$.

$^1$H NMR, $^{13}$C, and FTIR of KFUPM-HOF $^1$H NMR (DMSO-d$_6$): δ 7.36 (s, 4H, —NH$_2$), 8.65 (s, 3H, Ar—H), 8.66 (s, 1H, NH).

$^{13}$C NMR (DMSO-d$_6$): δ 133.2, 133.8, 155.9, and 167.2.

FTIR: 3389, 3153, 2430, 1640, 1608, 1546, 1430, 1398, 1330, 1221, 990, 901, 786, 749, 687 cm$^{-1}$.

$^1$H NMR, $^{13}$C, and FTIR of KFUPM-HOF-1

$^1$H NMR (DMSO-d$_6$) δ 6.59 (s, 2H, —NH$_2$), 6.37 (s, br, 4H, —NH$_2$), 7.04 (s, 3H, Ar—H), 8.01 (s, br, 4H, —NH$_2$), 8.62 (s, 3H, Ar—H), 8.64 (s, 3H, Ar—H).

$^{13}$C NMR (DMSO-d$_6$): δ 117.3, 132.7, 133.3, 133.8, 133.9, 164.1, 166.6, and 167.5.

FTIR: 3385, 3219, 3178, 3087, 2994, 1887, 1719, 1689, 1658, 1628, 1602, 1512, 1501, 1429, 1412, 1363, 1330, 1319, 1236, 1217, 1109, 971, 921, 893, 878, 811, 788, 745, 744 cm$^{-1}$.

$^1$H NMR, $^{13}$C, and FTIR of KFUPM-HOF-2

$^1$H NMR (DMSO-d$_6$) δ 6.37 (s, br, 4H, —NH$_2$), 6.59 (s, 4H, —NH$_2$), 7.04 (s, 4H, Ar—H), 8.01 (s, br, 3H, Ar—H), 8.62 (s, 3H, Ar—H), 8.64 (s, 3H, Ar—H).

$^{13}$C NMR (DMSO-d$_6$): δ 117.3, 132.7, 133.3, 133.8, 133.9, 164.1, 166.6, and 167.5.

FTIR: 3385, 3219, 3178, 3087, 2994, 1887, 1719, 1689, 1658, 1628, 1602, 1512, 1501, 1429, 1412, 1363, 1330, 1319, 1236, 1217, 1109, 971, 921, 893, 878, 811, 788, 745, 744 cm$^{-1}$.

Morphology and microstructure analysis of the HOFs was performed by conducting Powder X-Ray Diffraction (PXRD) pattern analysis, Fourier-Transform Infrared (FTIR) spectroscopy, Field Emission Scanning Electron Microscope (FESEM) imaging, and Thermogravimetric analysis (TGA).

Powder X-Ray Diffraction (PXRD) patterns of the samples were recorded using a Rigaku MiniFlex diffractometer, which was equipped with Cu Kα radiation. The data were acquired over the 2θ range of 5 and 60°.

PXRD measurements was conducted to determine the crystalline structures of the synthesized HOFs. As shown in FIG. 2A, FIG. 2B, and FIG. 2C, the diffractogram depicts crystalline HOF structures with barely any amorphous background as evident from their sharp reflections.

For KFUPM-HOF, the major peaks were observed at 7.2°, 15.7°, 19.5°, 21.3°, 26.2°, 27.4°, 29.2°, 38.2°, and 43.8°, of which the peak at 21.3° was the most intense peak. Some minor and rather broad reflections were also observed between 100 and 35°.

In case of KFUPM-HOF-1, five major reflections were observed at 6.3°, 13.5°, 18.4°, 18.7°, 23.8°, 27.6°, of which the peak at approximately 180 consisted of a doublet peak containing reflections at 18.4° and 18.7°. Some minor peaks were also observed between 150 and 45°.

The spectra of KFUPM-HOF-2 displayed several peaks at 15.5°, 19.3°, 20.8°, 21.4°, 21.8°, 24.0°, 26.2°, and 27.9°, of which the peaks at approximately 210 consisted of triplet having contributions from the reflections arising from three peaks at 20.8°, 21.4°, and 21.8°. The most intense peak was observed approximately 270 which consisted of a doublet arising from peaks at 26.2° and 26.8°.

No characteristic peaks for TMA, GZ, MA, or p-PD were observed in the spectra of any of the synthesized HOFs.

Field Emission Scanning Electron Microscope (FESEM, Tescan Lyra-3 Dual Beam instrument) equipped with an Energy Dispersion Spectrometer (EDX, Oxford Instruments) was used to discern the morphological features and confirm the constituent elements. The morphological features of the synthesized HOF structures were investigated by Field Emission Scanning Electron Microscopy (FE-SEM) and are depicted in FIGS. 3A-3I.

Figure 3A:
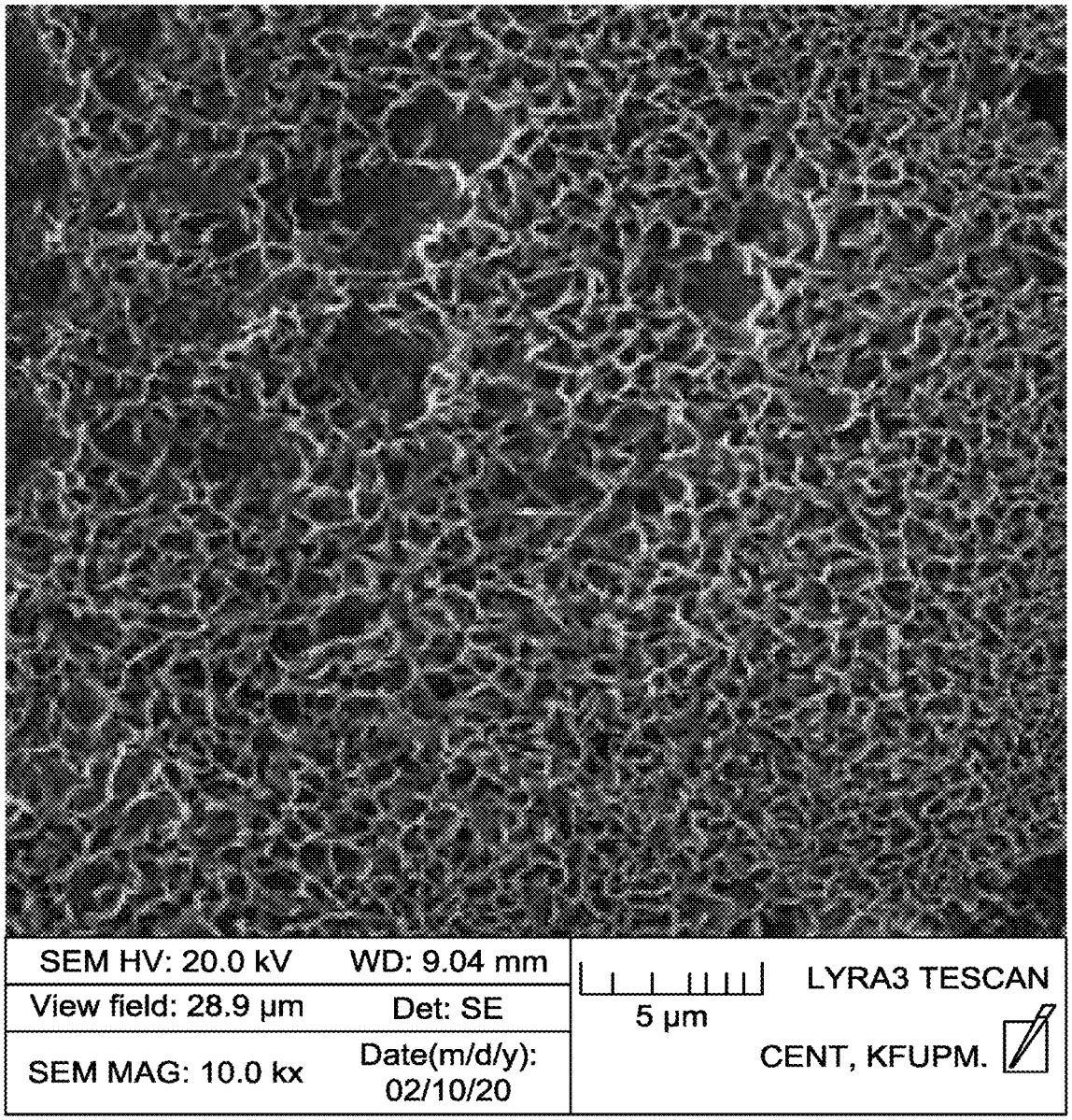
FIG. 3A shows FESEM image of KFUPM-HOF at 10 k× magnifications, according to certain embodiments.
Figure 3B:
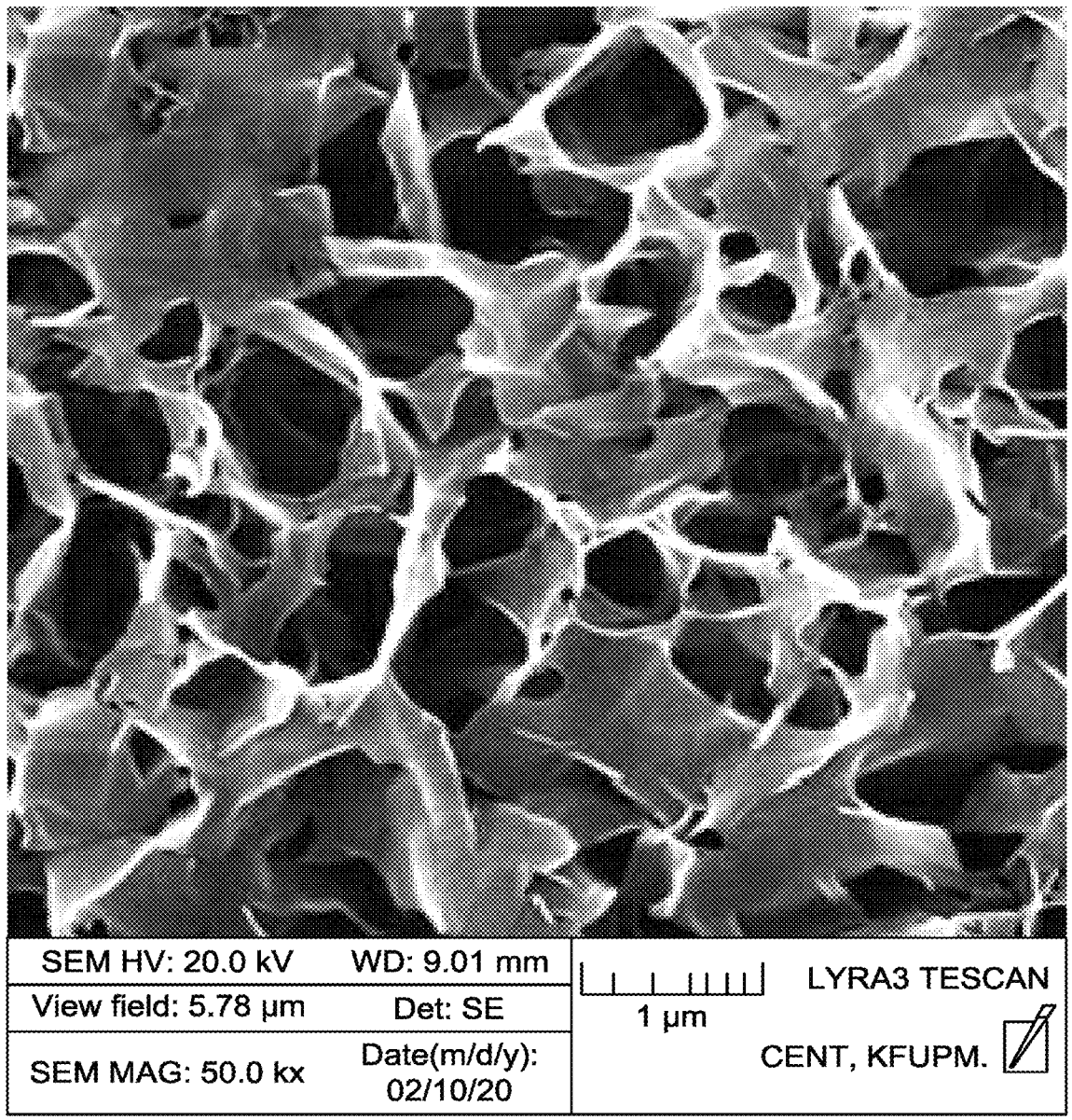
FIG. 3B shows FESEM image of KFUPM-HOF at 50 k× magnifications, according to certain embodiments.
Figure 3C:
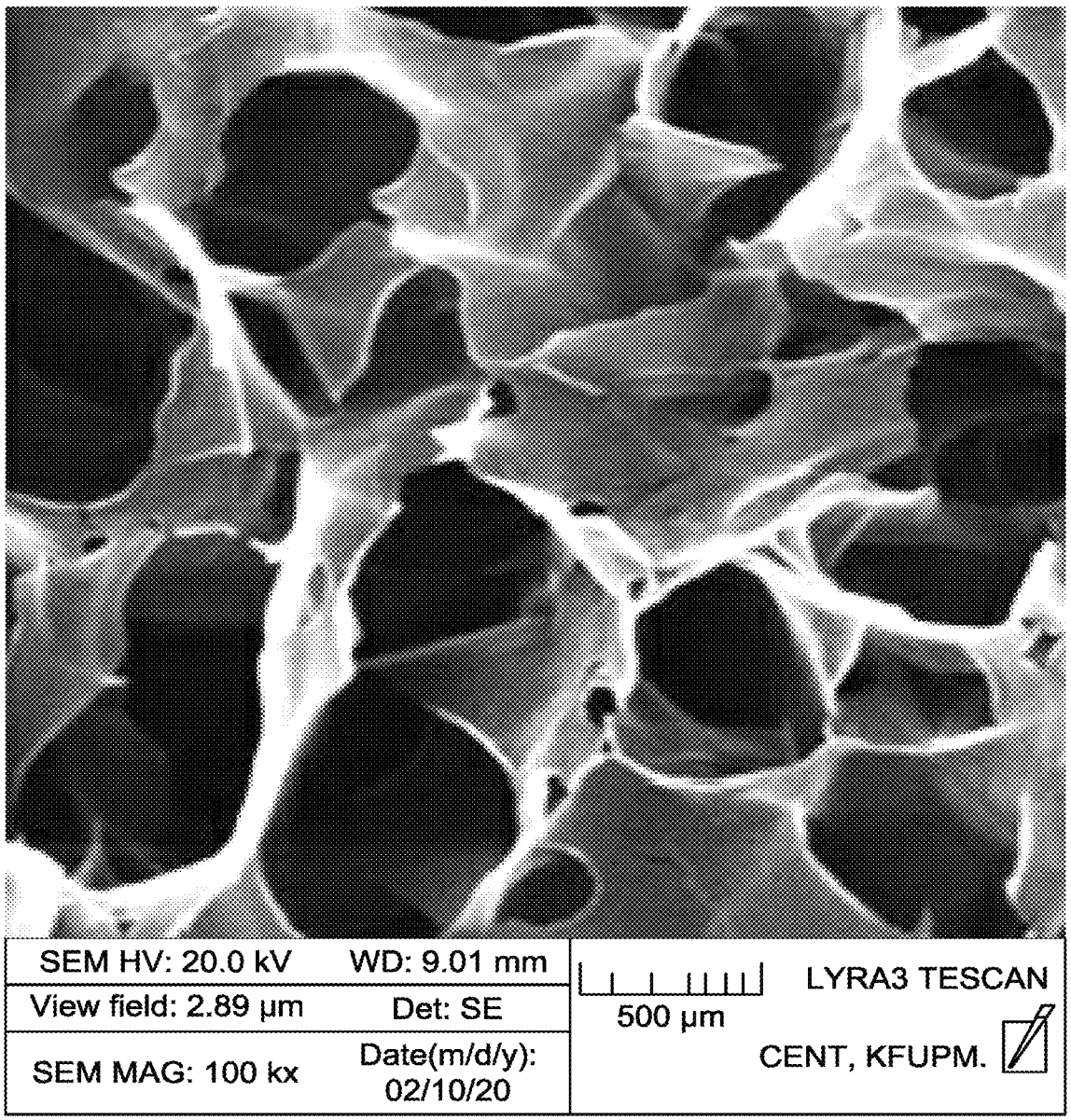
FIG. 3C shows FESEM image of KFUPM-HOF at 100 k× magnifications, according to certain embodiments.

A typical low-magnification micrograph of the as-synthesized KFUPM-HOF is depicted in FIG. 3A, which clearly reveals that the sample consists of hierarchical macroporous network of sheet-like structures with wide pores on the surface. Magnified images shown in FIG. 3B and FIG. 3C reveal the detailed structure of the porous network and clearly shows 2D sheets of thickness approximately 5-7 nm, intercrossed with each other.

Figure 3D:
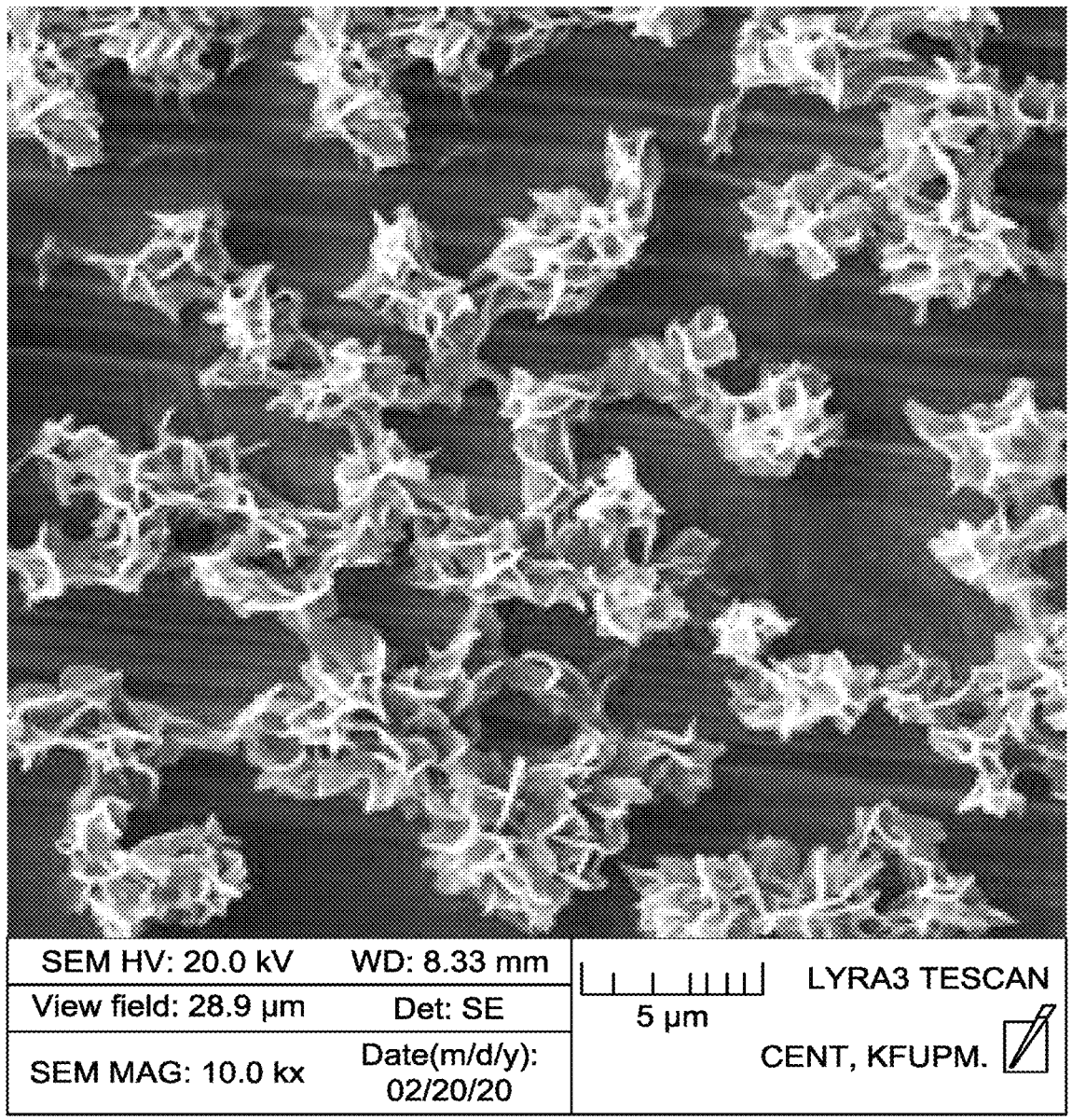
FIG. 3D shows FESEM image of KFUPM-HOF-1 at 10 k× magnifications, according to certain embodiments.
Figure 3E:
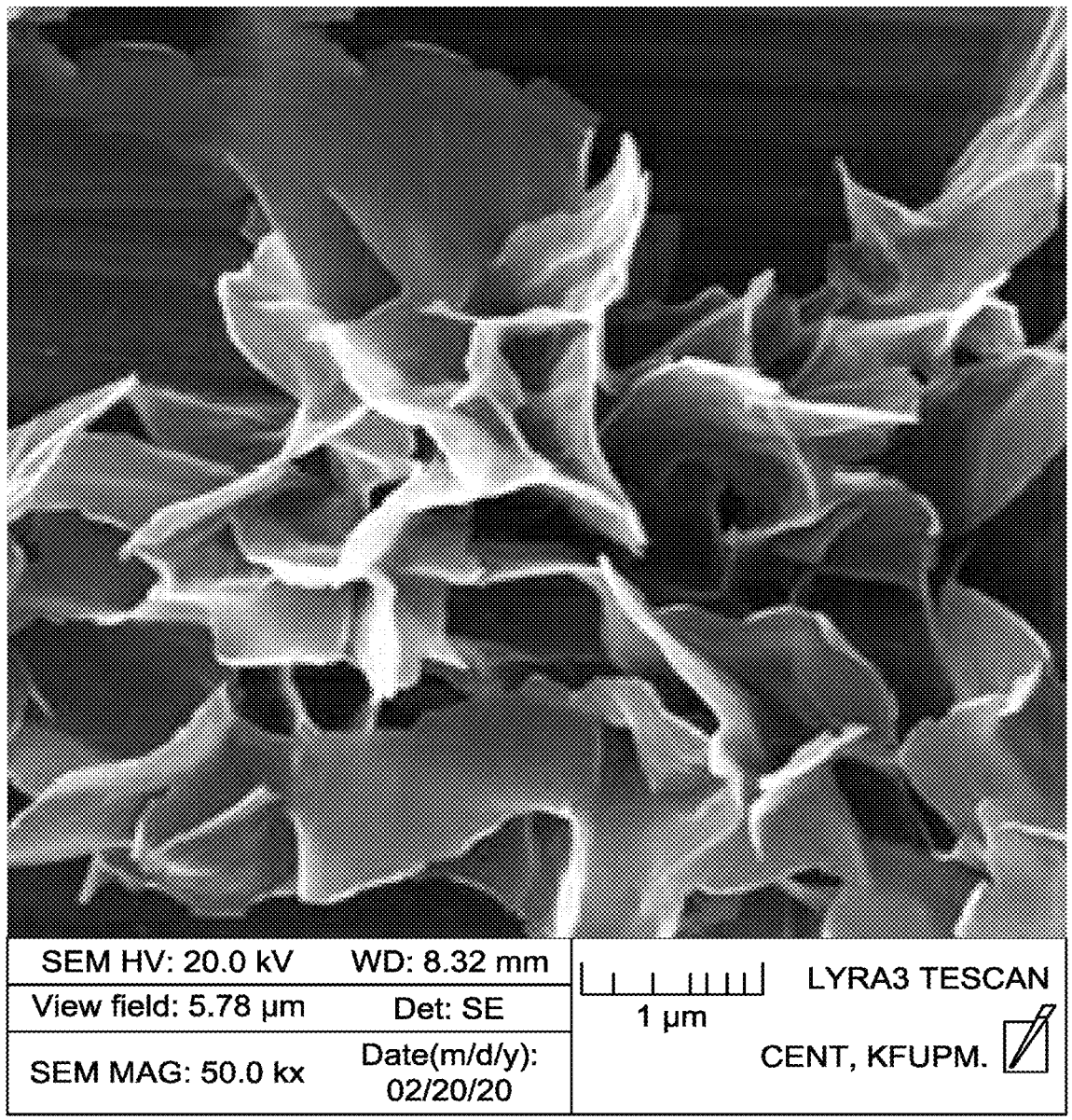
FIG. 3E shows FESEM image of KFUPM-HOF-1 at 50 k× magnifications, according to certain embodiments.
Figure 3F:
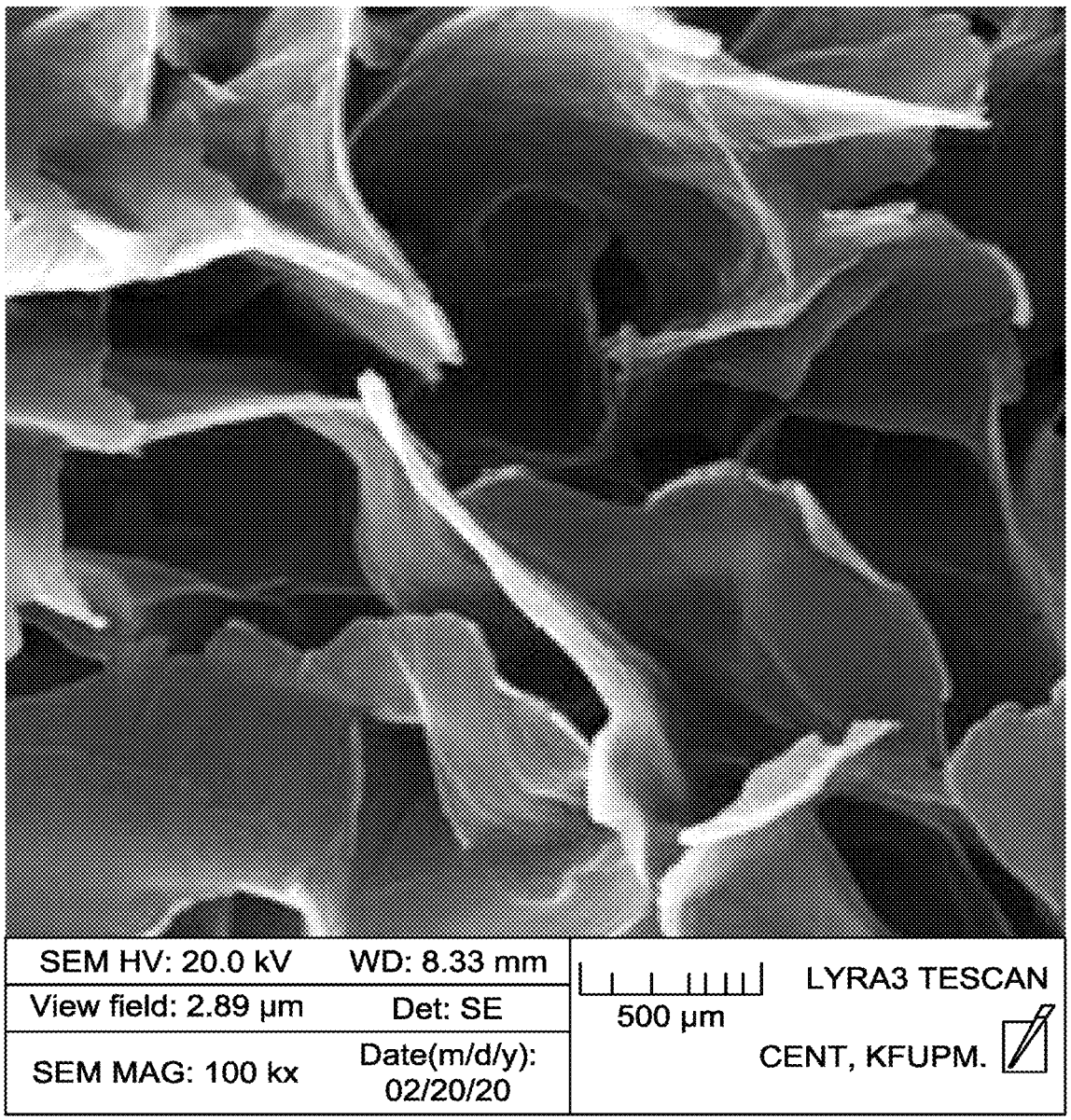
FIG. 3F shows FESEM image of KFUPM-HOF-1 at 100 k× magnifications, according to certain embodiments.

The morphological features of the as-synthesized KFUPM-HOF-1 are shown in FIG. 3D, FIG. 3E, and FIG. 3F. At low magnification, as shown in FIG. 3D, the sample consisted of micro flowers of size approximately 1 μm. A close observation of these structures at higher magnification revealed a uniform 2D-sheet like structures which are strikingly similar to those obtained for KFUPM-HOF except in thickness. Relatively thicker intercrossed and/or merging sheets, of approximately 30 nm assembled into flower like morphology, were observed, as seen in FIG. 3E and FIG. 3F.

Figure 3G:
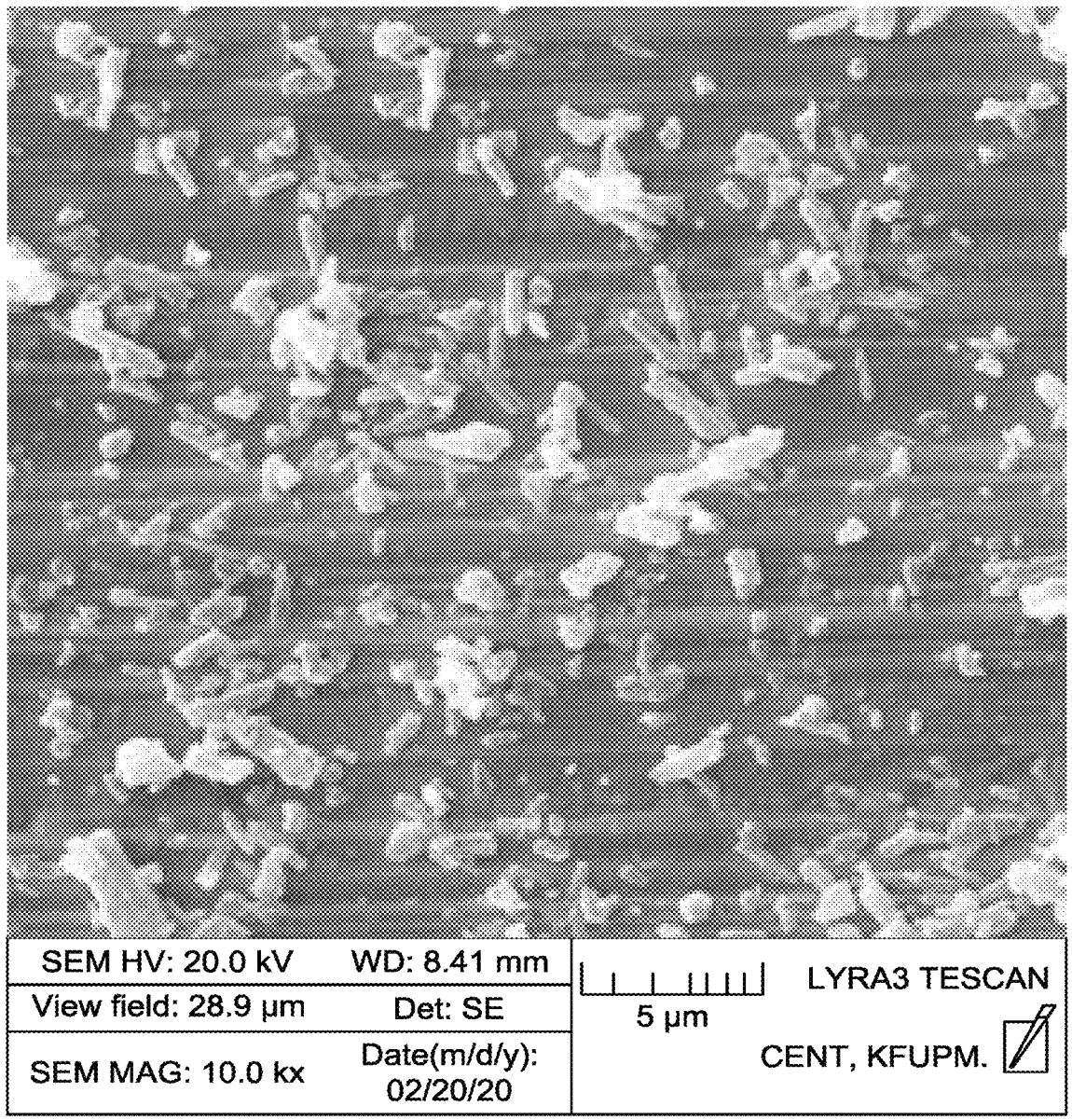
FIG. 3G shows FESEM image of KFUPM-HOF-2 at 10 k× magnifications, according to certain embodiments.
Figure 3H:
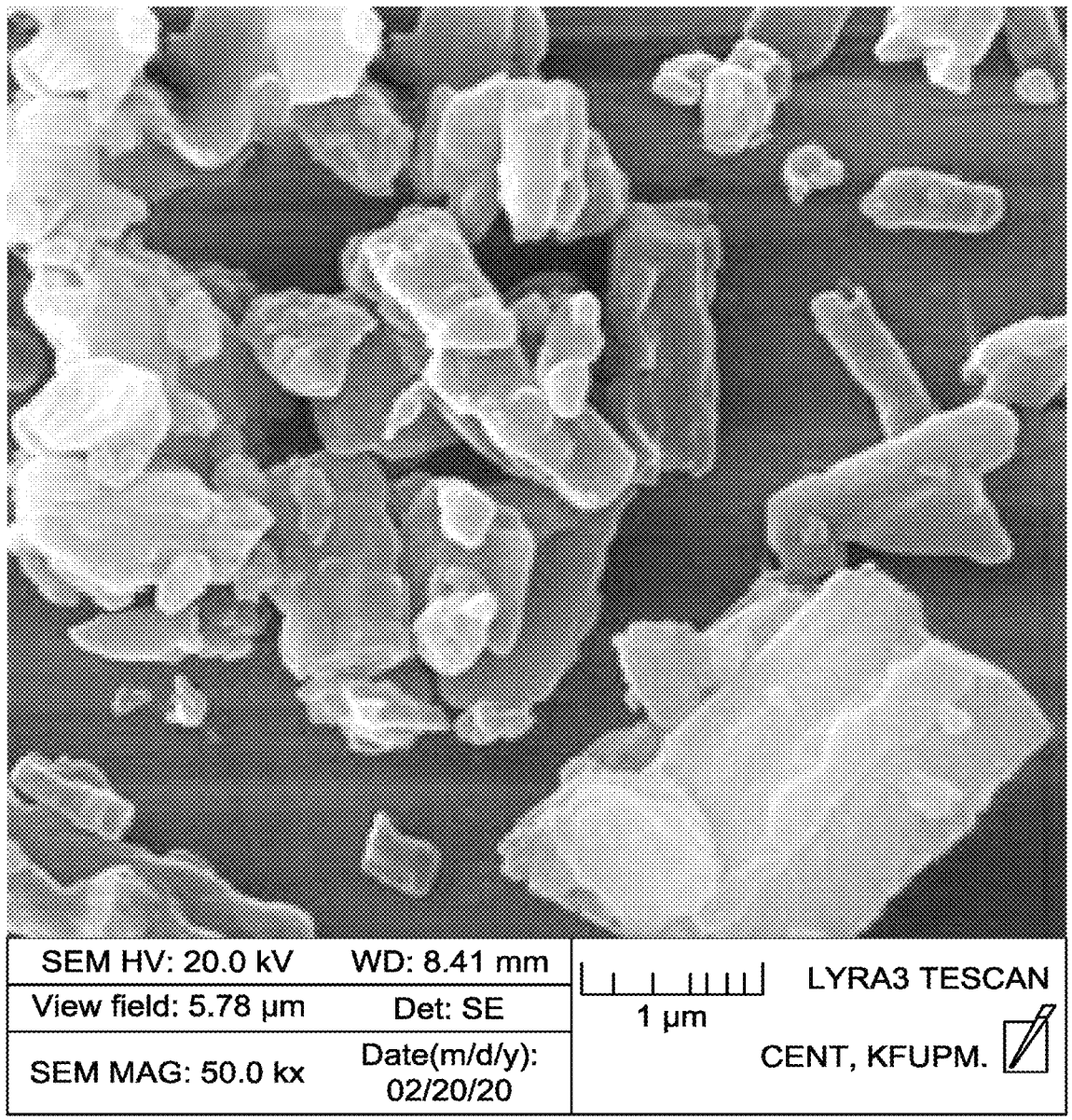
FIG. 3H shows FESEM image of KFUPM-HOF-2 at 50 k× magnifications, according to certain embodiments.
Figure 3I:
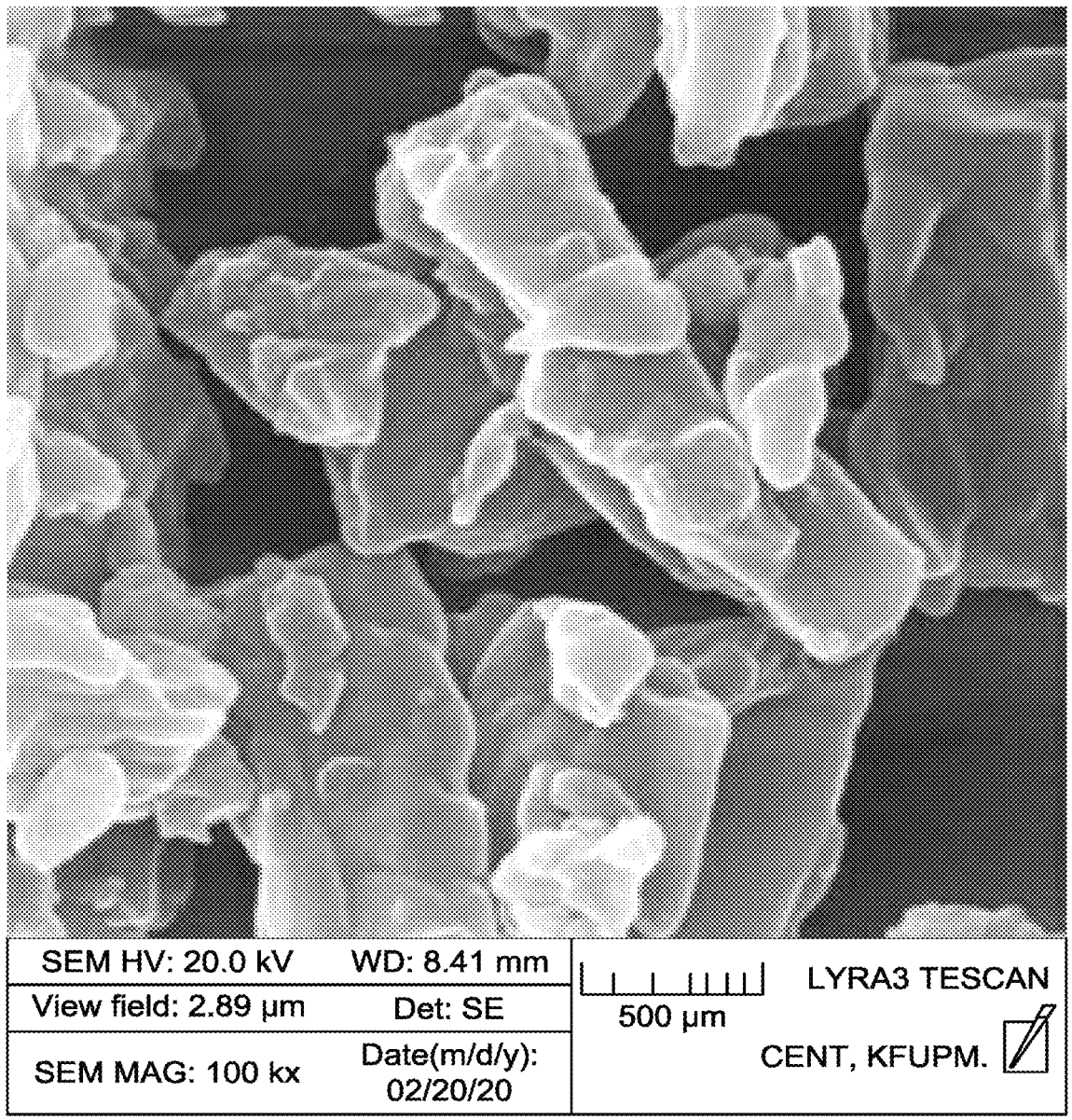
FIG. 3I shows FESEM image of KFUPM-HOF-2 at 100 k× magnifications, according to certain embodiments.

The micrographs of as-synthesized KFUPM-HOF-2, as seen in FIG. 3G, FIG. 3H, and FIG. 3I, revealed micro-rod like structures of varying length. A close observation of these structures revealed that each rod consisted of fused sheet like structures, as observed in FIG. 3H and FIG. 3I.

Figure 4A:
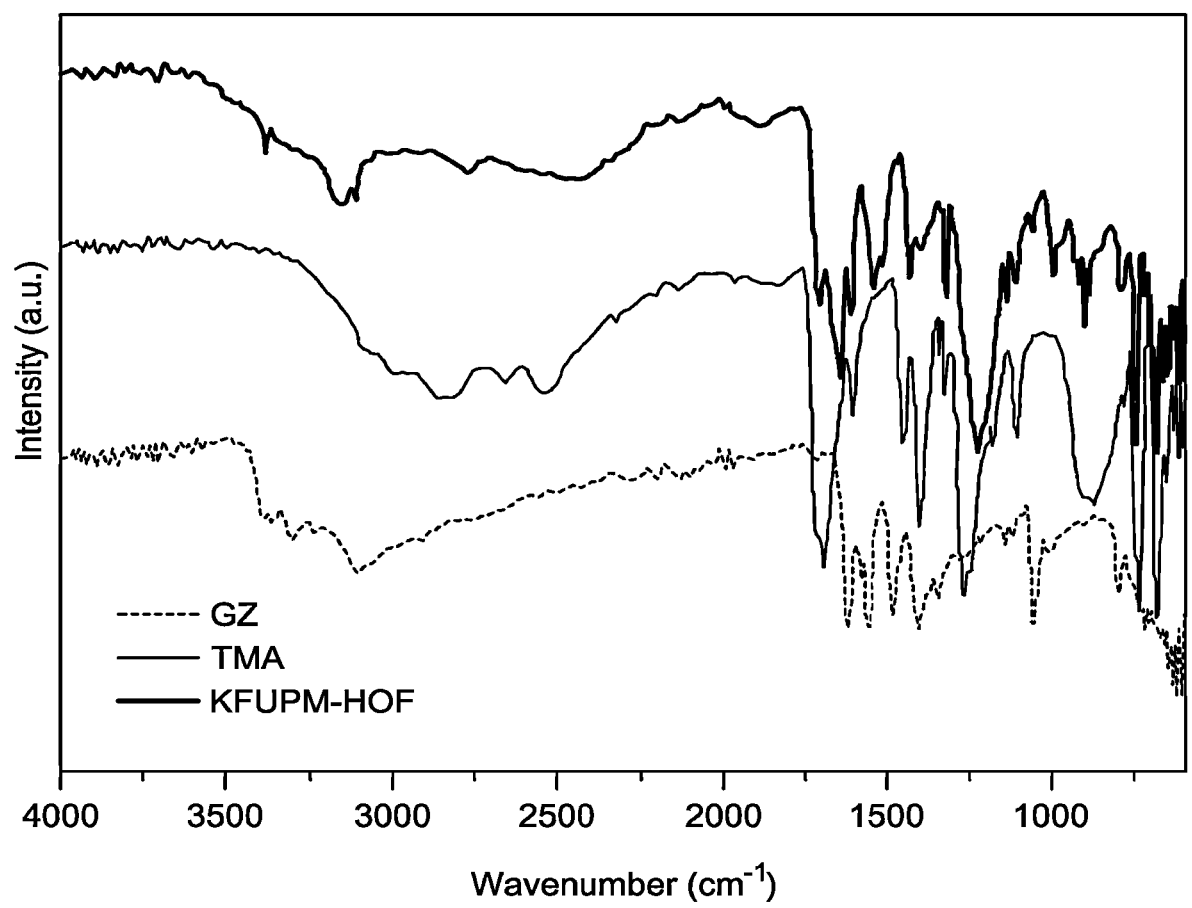
FIG. 4A shows FTIR plot of TMA, GZ, and KFUPM-HOF, according to certain embodiments.
Figure 4B:
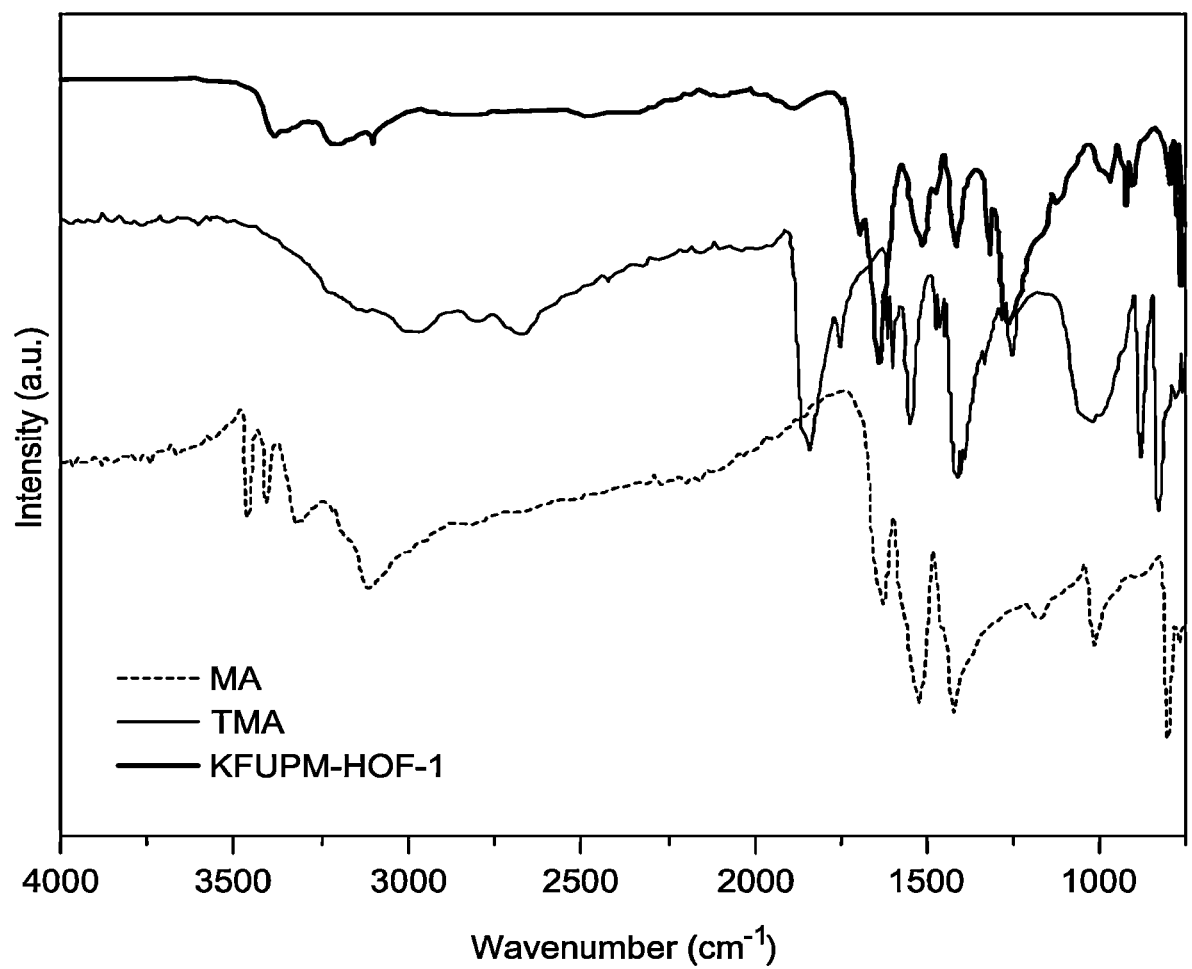
FIG. 4B shows FTIR plot of TMA, MA, and KFUPM-HOF-1, according to certain embodiments.
Figure 4C:
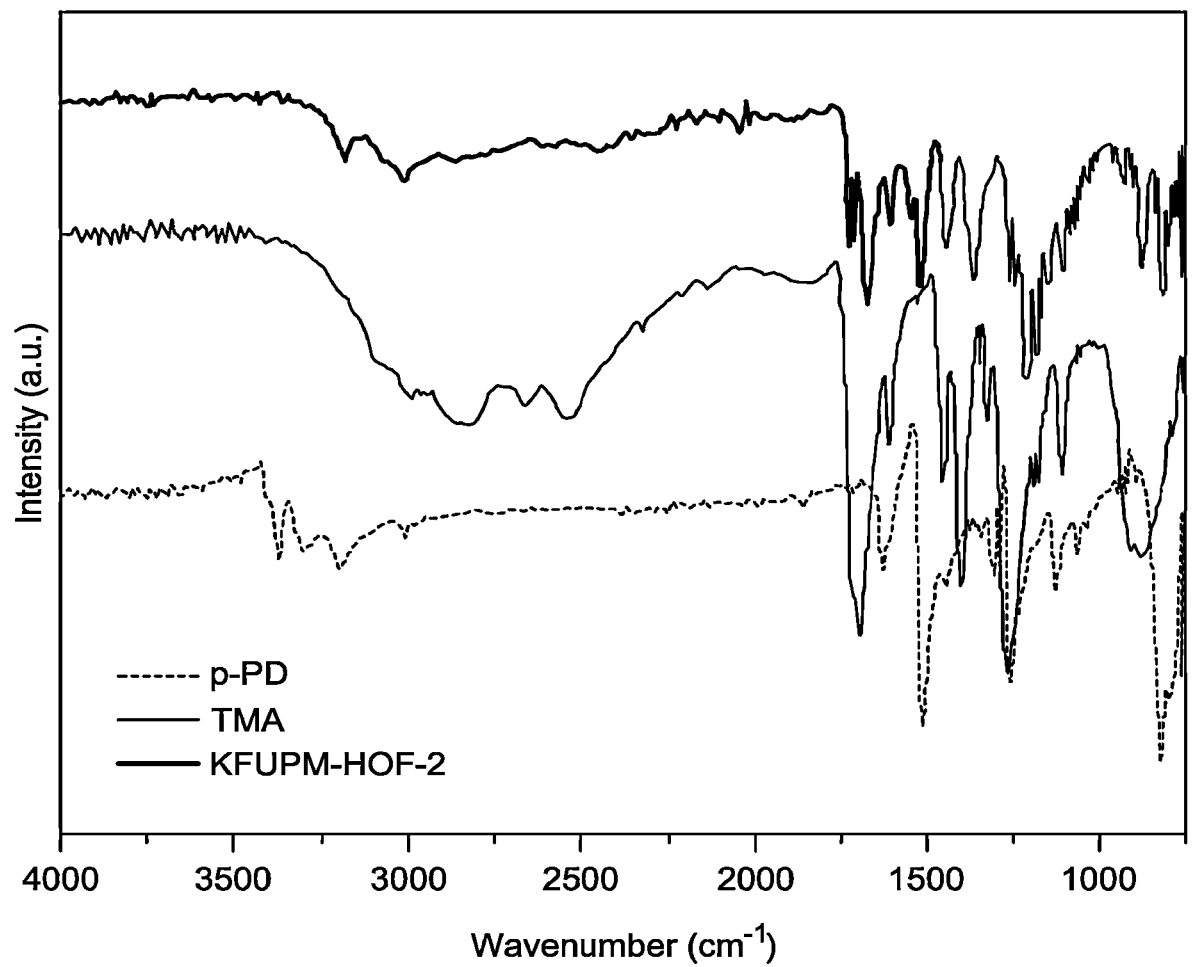
FIG. 4C shows FTIR plot TMA, p-PD, and KFUPM-HOF-2, according to certain embodiments.

The Fourier-Transform Infrared (FTIR) spectra is shown in FIG. 4A, FIG. 4B, and FIG. 4C. The FTIR analysis of GZ, TMA, and KFUPM-HOF reveals several distinct peaks of acid and amine both in KFUPM-HOF (FIG. 4A). It is observed that the NH stretching vibration peak at 3383 cm$^{-1}$ for the amine is found at 3389 cm$^{-1}$ for the KFUPM-HOF. The NH stretching vibration of the amino group at 3096 cm$^{-1}$ is shifted to 3153 cm$^{-1}$ for KFUPM-HOF due to hydrogen bonding with the aromatic tricarboxylic acid. The strong OH stretching vibration peak of the acid at 2813 cm$^{-1}$ and 2535 cm$^{-1}$ are shifted to 2430 cm$^{-1}$ due to hydrogen bonding between the GZ and the TMA. In TMA, the peak at 1692 cm$^{-1}$ is shifted to 1640 cm$^{-1}$ is due to its participation in the hydrogen bonding with the amine. The peak at 1619 cm$^{-1}$ in the amine corresponding to the out of plane bending of NH$_2$ and the stretching vibration of the CN bond is observed at 1608 cm$^{-1}$ in case of KFUPM-HOF. The peak at 1556 cm$^{-1}$ in the GZ is due to the out of plane bending of CNH and NH$_2$ bond which is observed in KFUPM-HOF at 1546 cm$^{-1}$ confirming the presence of the amine in it. Furthermore, the stretching vibration of the ring CN bond in the GZ at 1477 cm$^{-1}$ is also observed in KFUPM-HOF at 1430 cm$^{-1}$ due to hydrogen bonding.

It may be noted that the amine GZ usually exists in two tautomeric forms GZ I and GZ II, as shown below.

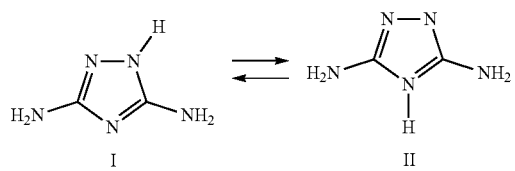

In case of the free amine, the peaks of the NH$_2$ are at 4.81 ppm and 5.51 ppm, due to its asymmetric nature, and the NH peak is at 10.74 ppm. In the formation of the KFUPM-HOF with the TMA and GZ through hydrogen bonding between the hydrogen of the NH$_2$ and the oxygen of the carboxylic acid, the peaks of the two $NH_2$ are shifted downfield to 7.36 ppm from 4.81 ppm and 5.51 ppm due to deshielding. Moreover, it is evident from the both $^1H$ and $^{13}C$ NMR of KFUPM-HOF (see above) that the tautomer II is more stable, that results in a symmetric amine and one broad peak at 7.36 ppm for the two $NH_2$ group. In case of the NH proton of the amine ring (8.66 ppm), it is merged with the TMA peak (8.65 ppm) due to the tautomeric form GZ II.

All the thermogravimetric mass loss profile curves were collected using a Metler-Toledo TGA. The samples were loaded into an alumina crucible and the mass loss profile was collected under a constant Ar-flow of 20 mL min$^{-1}$ at a constant ramp rate of 10° C. min$^{-1}$.

Figure 5A:
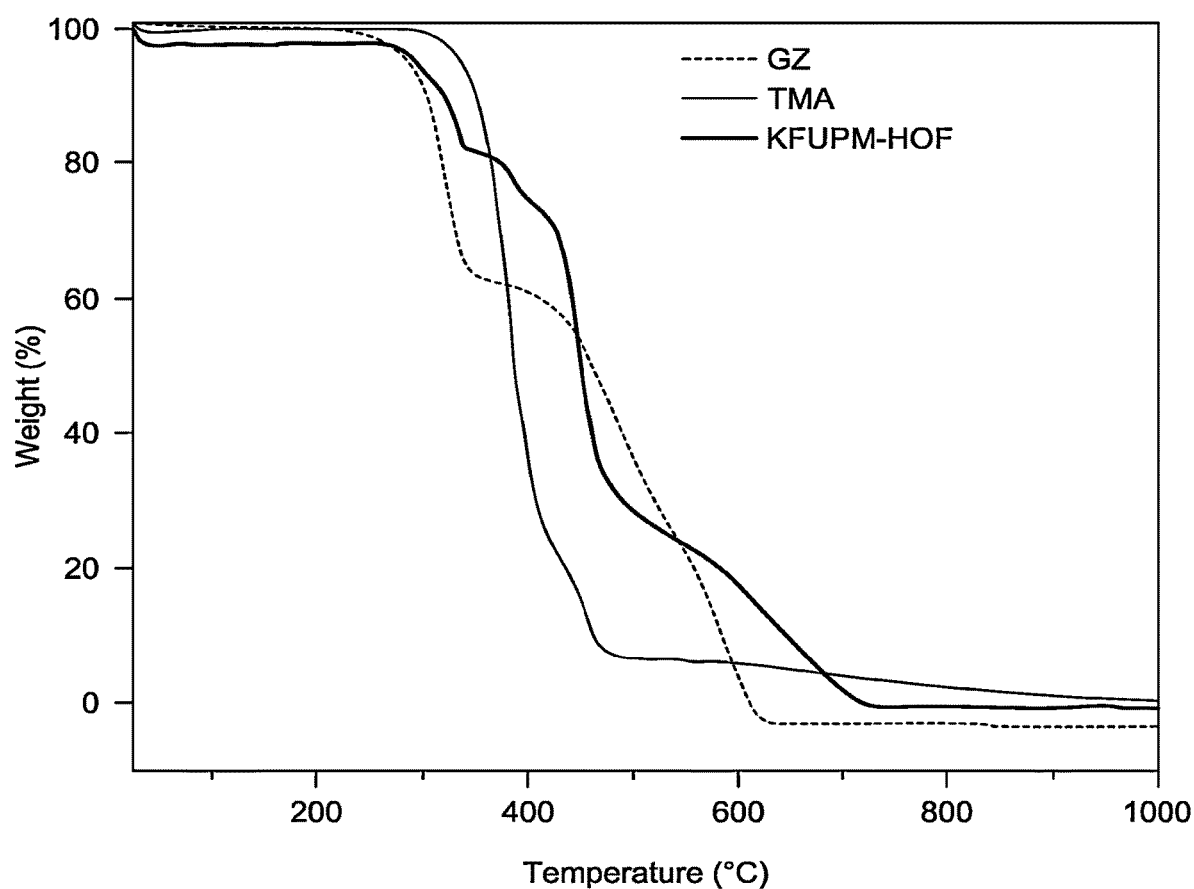
FIG. 5A shows TGA plot of TMA, GZ, and KFUPM-HOF, according to certain embodiments.
Figure 5B:
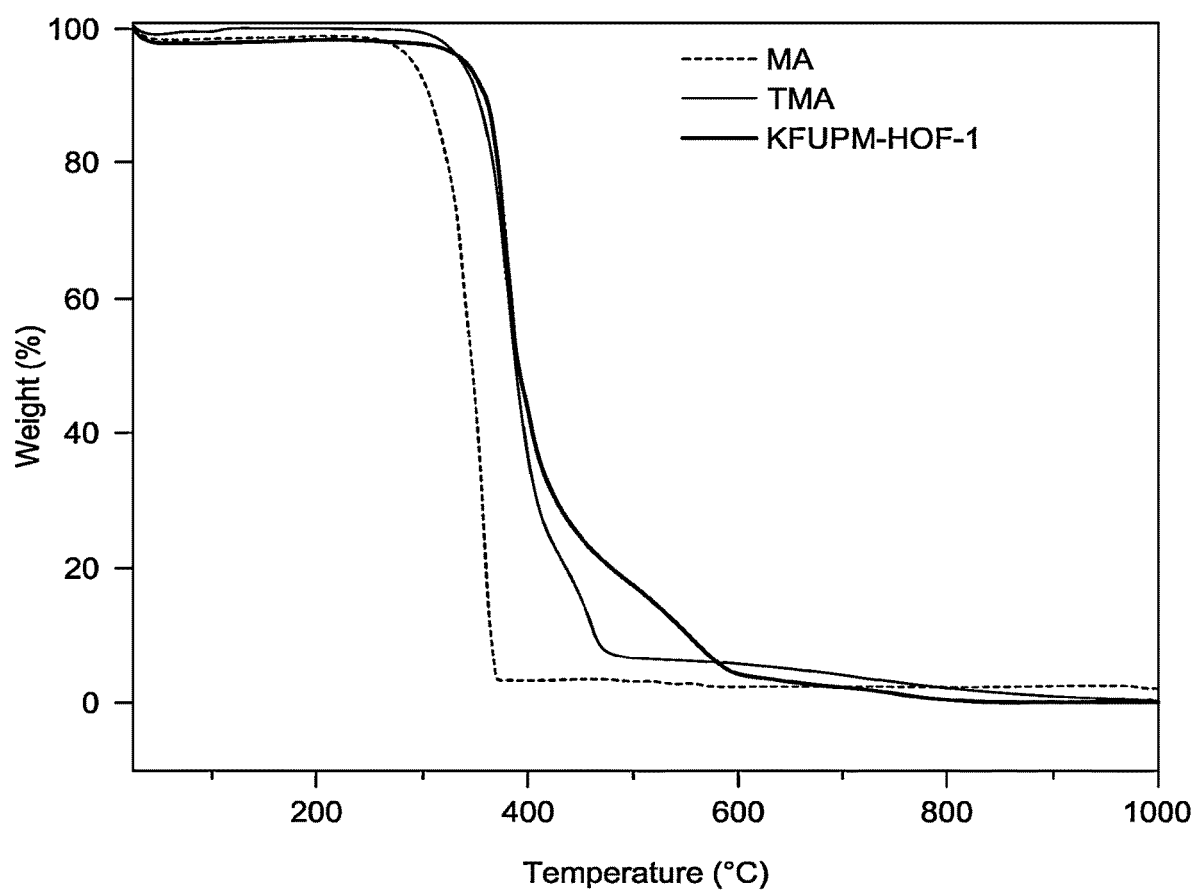
FIG. 5B shows TGA plot of TMA, MA, and KFUPM-HOF-1, according to certain embodiments.
Figure 5C:
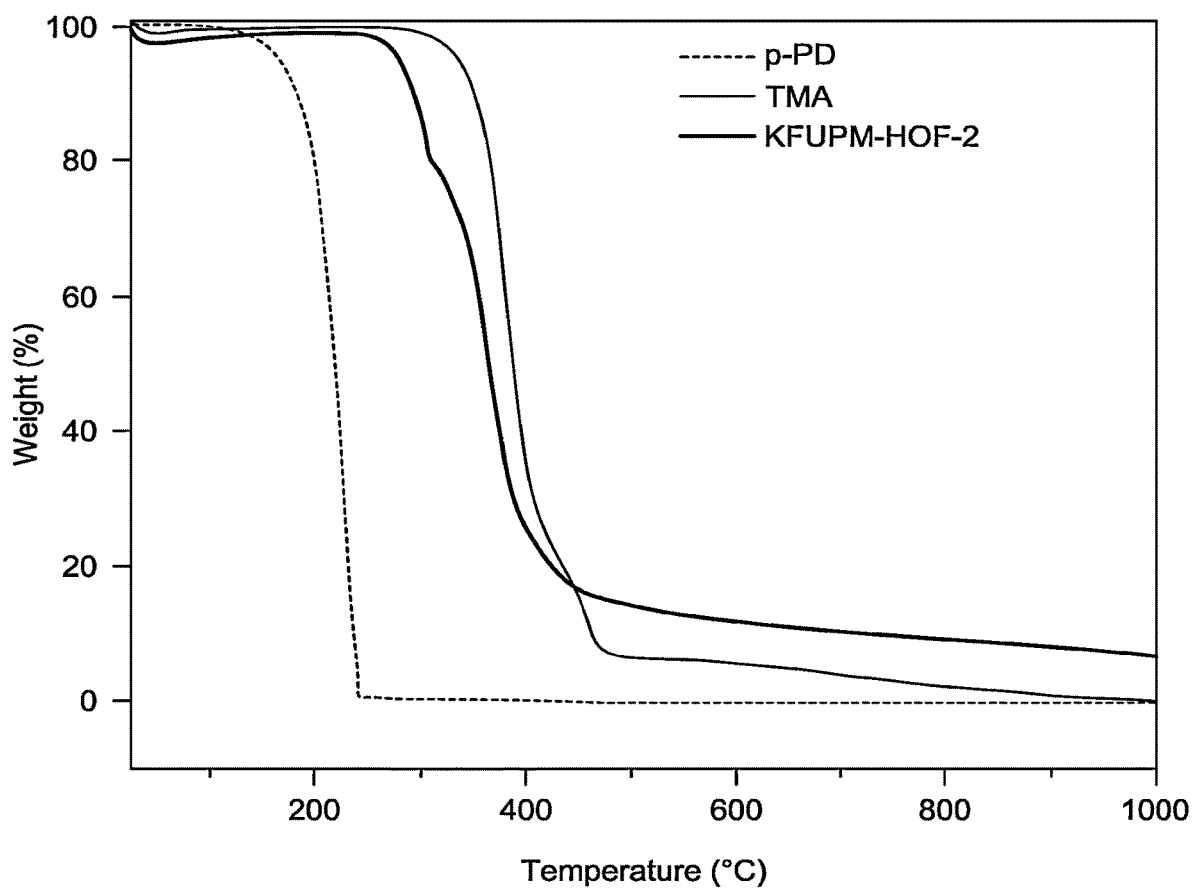
FIG. 5C shows TGA plot of TMA, p-PD, and KFUPM-HOF-2, according to certain embodiments.

Thermogravimetric analysis (TGA) was used to compare the mass-loss profiles of the precursors and the resultants HOF structures under $N_2$ flow, and the curves are presented in FIG. 5A, FIG. 5B, and FIG. 5C. Two weight loss stages are observed for all the HOFs except KFUPM-HOF-2 which exhibited weight loss in almost one stage as illustrated in FIG. 5C. The initial weight loss of 1-3% at 100-120° C. could be likely due to the presence of moisture in the HOF network while thermal degradation of the KFUPM-HOF network accounts for the second weight loss which starts at approximately 280° C. which is higher than the GZ and lower than TMA as shown in FIG. 5A. The different thermal behavior is observed between the KFUPM-HOF and its precursors clearly show that the HOF is developed constructed by intermolecular hydrogen bonding. The analogous behaviors are observed in other resultant HOFs (KFUPM-HOF-1 and KFUPM-HOF-2), as revealed in FIG. 5B and FIG. 5C. The TGA curves show that the thermal decomposition temperatures of HOFs are in the following order: 320° C. (KFUPM-HOF-1)>280° C. (KFUPM-HOF)>260° C. (KFUPM-HOF-2) which could be due to the thermal decomposition of their respective amine precursors. The thermal decomposition temperature of amine precursors viz. MA, GZ, and p-PD, is found to be 280° C., 260° C., and 160° C., respectively.

Highly crystalline HOFs were synthesized using only water as a solvent. Varying the carboxylic acid compound and aromatic compound components of the HOF resulted in different properties and morphologies. Therefore, this method could be used to synthesize a variety of HOFs.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A one-pot method of making a hydrogen-bonded organic framework (HOF), comprising:
    dissolving trimesic acid in water at a temperature greater than 60° C. to form a first solution;
    dissolving an aromatic compound in water to form a second solution wherein the aromatic compound is substituted with at least two amine groups;
    adding dropwise the second solution into the first solution at a temperature greater than 60° C. to form a synthetic solution;
    cooling the synthetic solution to below 50° C. forming a precipitate; and
    separating and drying the precipitate at a temperature of at least 60° C. to yield the HOF;
    wherein the first and second solutions do not comprise an organic solvent.

2. The method of claim 1, wherein the first solution consists of water and trimesic acid.

3. The method of claim 1, wherein the second solution consists of water and the aromatic compound.

4. The method of claim 1, wherein the aromatic compound is selected from a group consisting of guanazole, melamine and p-phenylenediamine.

5. The method of claim 1, having an aromatic compound to trimesic acid molar ratio of 1:1 to 5:1.

6. The method of claim 1, wherein the temperature of the first solution during the dropwise addition of the second solution does not vary by more than 5° C.

7. The method of claim 1, wherein the first solution during the dropwise addition of the second solution is stirred at a rate of 600-800 rpm.

8. The method of claim 1, wherein the HOF is substantially crystalline.

9. The method of claim 1, wherein the HOF does not comprise non hydrogen-bonded aromatic compound.

10. The method of claim 1, wherein:
    the aromatic compound is guanazole; and
    the HOF has a sheet structure;
    wherein the sheets form an intercrossed macroporous network with pores on a surface.

11. The method of claim 8, wherein the sheets have a thickness of 3-10 nm.

12. The method of claim 8, wherein the pores have a diameter of 300-800 nm.

13. The method of claim 8, wherein the HOF is stable up to 320° C.

14. The method of claim 1, wherein:
    the aromatic compound is melamine; and
    the HOF has a sheet structure;
    wherein the sheets form a flower morphology.

15. The method of claim 12, wherein the sheets have a thickness of 25-40 nm.

16. The method of claim 12, wherein the flowers have a diameter of 1-5 μm.

17. The method of claim 12, wherein the HOF is stable up to 280° C.

18. The method of claim 1, wherein:
    the aromatic compound is p-phenylenediamine;
    the HOF has a rod morphology;
    wherein the rods comprise fused sheets.

19. The method of claim 16, wherein the rods having a length of 0.5-4 μm.

20. The method of claim 16, wherein the rods having a width of 200-600 nm.

* * * * *